(12) United States Patent
Berman et al.

(10) Patent No.: US 7,474,732 B2
(45) Date of Patent: *Jan. 6, 2009

(54) CALIBRATION OF X-RAY REFLECTOMETRY SYSTEM

(75) Inventors: David Berman, Kiryat Tivon (IL); Asher Peled, Kfar Vradim (IL); Dileep Agnihotri, Round Rock, TX (US); Tachi Rafaeli, Givat Shimshit (IL); Boris Yokhin, Nazareth Illit (IL)

(73) Assignee: Jordan Valley Applied Radiation Ltd., Migdal Ha'emek (IL)

( * ) Notice: Subject to any disclaimer, the term of this patent is extended or adjusted under 35 U.S.C. 154(b) by 313 days.

This patent is subject to a terminal disclaimer.

(21) Appl. No.: 11/000,044

(22) Filed: Dec. 1, 2004

(65) Prior Publication Data

US 2006/0115046 A1    Jun. 1, 2006

(51) Int. Cl.
G01N 23/20 (2006.01)
H05G 1/64 (2006.01)
A61B 6/08 (2006.01)

(52) U.S. Cl. .................. 378/70; 378/98.8; 378/205
(58) Field of Classification Search .................. 378/70, 378/71, 81–90, 98.8, 205, 207
See application file for complete search history.

(56) References Cited

U.S. PATENT DOCUMENTS

| | | | |
|---|---|---|---|
| 4,725,963 A | 2/1988 | Taylor et al. | |
| 4,989,226 A | 1/1991 | Woodbury et al. | |
| 5,151,588 A | 9/1992 | Kiri et al. | |
| 5,574,284 A | 11/1996 | Farr | |
| 5,619,548 A | 4/1997 | Koppel | |
| 5,740,226 A | 4/1998 | Komiya et al. | |
| 5,949,847 A | 9/1999 | Terada et al. | |
| 5,963,329 A | 10/1999 | Conrad et al. | |
| 6,041,098 A | 3/2000 | Touryanski et al. | |
| 6,192,103 B1 | 2/2001 | Wormington et al. | |
| 6,226,347 B1 | 5/2001 | Golenhofen | |
| 6,226,349 B1 | 5/2001 | Schuster et al. | |
| 6,381,303 B1 | 4/2002 | Vu et al. | |
| 6,389,102 B2 | 5/2002 | Mazor et al. | |
| 6,453,006 B1 | 9/2002 | Koppel et al. | |
| 6,507,634 B1 | 1/2003 | Koppel et al. | |

(Continued)

FOREIGN PATENT DOCUMENTS

JP        9-308339        12/1997

(Continued)

OTHER PUBLICATIONS

Wiener et al., "Characterization of Titanium Nitride Layers by Grazing-Emission X-Ray Fluorescence Spectrometry", in Applied Surface Science 125 (1998), p. 129-136.

(Continued)

*Primary Examiner*—Irakli Kiknadze
(74) *Attorney, Agent, or Firm*—Smith, Gambrell & Russell, LLP

(57) ABSTRACT

A method for inspection of a sample includes irradiating the sample with a beam of X-rays and measuring a distribution of the X-rays that are emitted from the sample responsively to the beam, thereby generating an X-ray spectrum. An assessment is made of an effect on the spectrum of a non-uniformity of the beam, and the spectrum is corrected responsively to the effect.

108 Claims, 11 Drawing Sheets

U.S. PATENT DOCUMENTS

| | | | |
|---|---|---|---|
| 6,512,814 | B2 | 1/2003 | Yokhin et al. |
| 6,556,652 | B1 | 4/2003 | Mazor et al. |
| 6,639,968 | B2 | 10/2003 | Yokhin et al. |
| 6,643,354 | B2 | 11/2003 | Koppel et al. |
| 6,680,996 | B2 | 1/2004 | Yokhin et al. |
| 6,711,232 | B1 | 3/2004 | Janik |
| 6,744,950 | B2 | 6/2004 | Aleksoff |
| 6,750,952 | B2 | 6/2004 | Grodnensky et al. |
| 6,771,735 | B2 | 8/2004 | Janik et al. |
| 2001/0028699 | A1 | 10/2001 | Iwasaki |
| 2001/0043668 | A1 | 11/2001 | Hayashi et al. |
| 2002/0097837 | A1 | 7/2002 | Fanton et al. |
| 2002/0110218 | A1 | 8/2002 | Koppel et al. |
| 2003/0157559 | A1 | 8/2003 | Omote et al. |
| 2004/0052330 | A1 | 3/2004 | Koppel et al. |
| 2004/0156474 | A1 | 8/2004 | Yokhin et al. |
| 2004/0218717 | A1 | 11/2004 | Koppel et al. |

OTHER PUBLICATIONS

Hayashi et al., "Refracted X-Rays Propagating Near the Surface under Grazing Incidence Condition", Spectrochimica Acta, Part B 54, 1999, pp. 227-230.

Series 5000 Model XTF5011 X-Ray Tube Information, Oxford Instruments Inc., Scotts Valley, GA, U.S.A., Jun. 1998.

Monolithic Polycapillary Lens Information, X-Ray Optical Systems, Inc., Albany, NY, U.S.A., Dec. 29, 1998. (web site: www.xos.com).

S. Di Fonzo et al., "Non-Destructive Determination of Local Strain with 100-Nanometre Spatial Resolution", Nature, vol. 403, Feb. 10, 2000. (web site: www.nature.com).

Hugues Guerault, "Specular reflectivity and off-specular scattering", Tools for roughness investigation, Dec. 2000.

Jones, et al., "Small angle x-ray scattering for sub-100 nm pattern characterization", Applied Physics Letters 83:19 (2003), pp. 4059-4061.

Hu et al., "Small angle x-ray scattering metrology for sidewall angle and cross section of nanometer scale line gratings", Journal of Applied Physics 96:4 (2004), pp. 1983-1987.

Wu et al., "Small angle neutron scattering measurements of nanoscale lithographic features", Journal of Applied Physics 88:12 (2000), pp. 7298-7303.

Kojima, et al., "Structural characterization of thin films by x-ray reflectivity", Rigaku Journal 16:2 (1999), pp. 31-41.

Stommer, "X-ray scattering from silicon surfaces", in Semiconductor International (May 1, 1998).

Yoneda, "Anomalous surface reflection of X Rays", Physical Review 131, pp. 2010-2013, 1963.

Stommer, et al., "Characterization of semiconductor materials by X-ray scattering", Electrochemical Society Proceedings vol. 99-16, pp. 117-133, 1999.

Bowen, et al., "X-Ray metrology by diffraction and reflectivity", Characterization and Metrology for ULSI Technology, 2000 International Conference (American Institute of Physics, 2001). pp. 570-579.

Ulyanekov, "Introduction to high resolution X-Ray diffraction", Workshop on X-ray characterization of thin layers (Uckley, May 21-23, 2003).

Ito, "X-ray Scattering Method for Determining Pore-Size Distribution in Low-k Thin Films", Presented at the International Sematech Ultra-Low-k Workshop (San Francisco, CA, Jun. 6-7, 2002).

Naudon, et al., "New apparatus for grazing X-ray reflectometry in the angle-resoived dispresive mode", J. Appl. Cryst. 1989, vol. 22, pp. 460-464.

N. Wu, et al, "Substepping and its Application to HST Imaging", Jul. 28, 2003.

Wormington, Characterization of Pore Size Distribution in Low k Dielectrics Using X-ray Reflectivity, presented at the Sematech Gate Stack Engineering Workshop (Austin, Texas, May 2, 2002).

J. Spear, "Metrology for low-k materials", Silknet Aliance, 2003.

J.R. Levine Parrill, et al, "GISAXS—Glancing Incidence Small Angle X-ray Scattering", Journal de Physique IV 3 (Dec. 1993), pp. 411-417.

Jaklevic, et al., "High Rate X-Ray Fluorescence Analysis by Pulsed Excitation", IEEE Transactions on Nuclear Science NS-19:3 (1972), pp. 392-395.

Jaklevic, et al., "Small X-Ray Tubes for Energy Dispersive Analysis Using Semiconductor Spectrometers", Advances in X-Ray Analysis 15 (1972), pp. 266-275.

Jaklevic, et al., "Energy Dispersive X-Ray Fluorescence Spectrometry Using Pulsed X-Ray Excitation", Advances in X-Ray Analysis 19 (1976).

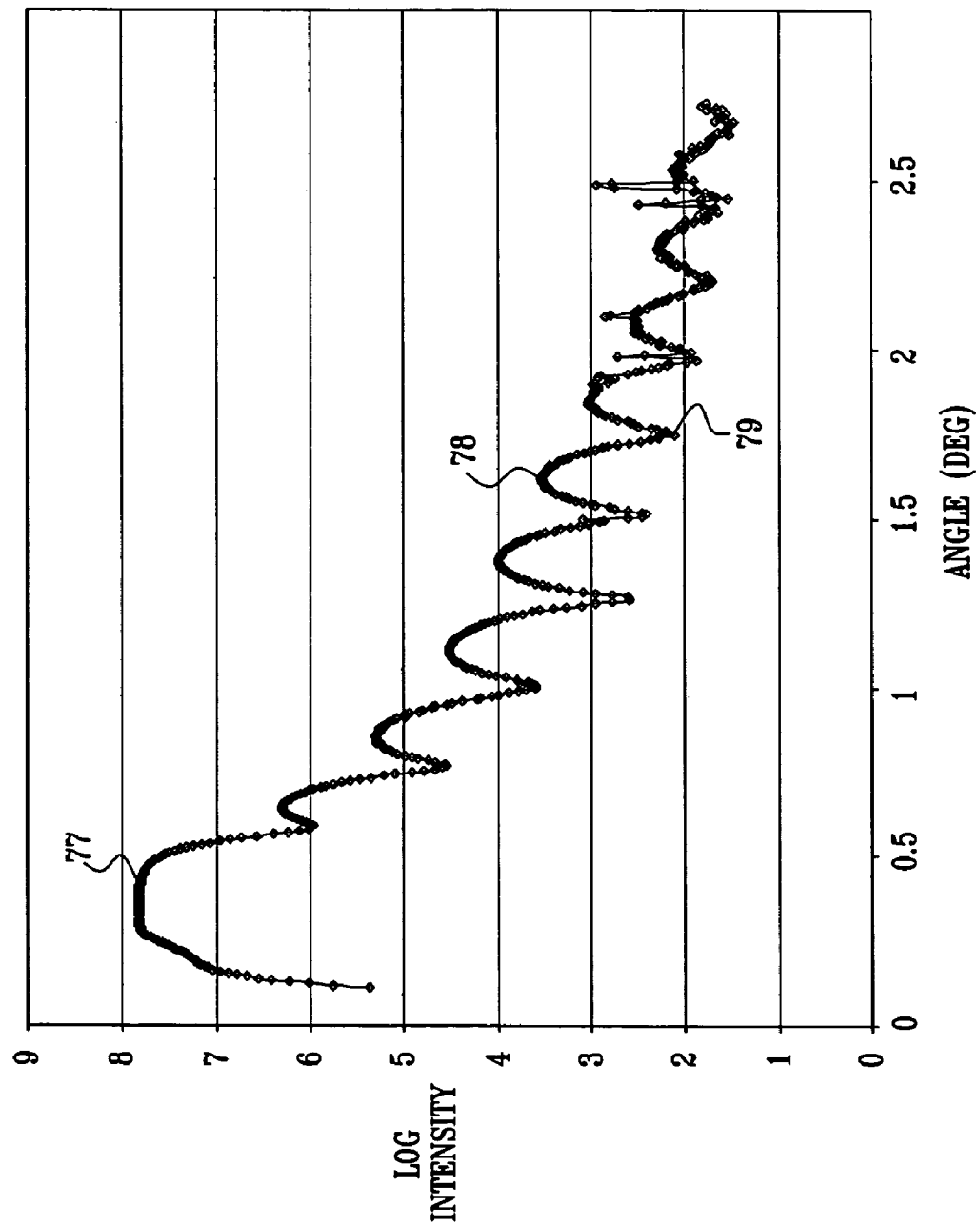

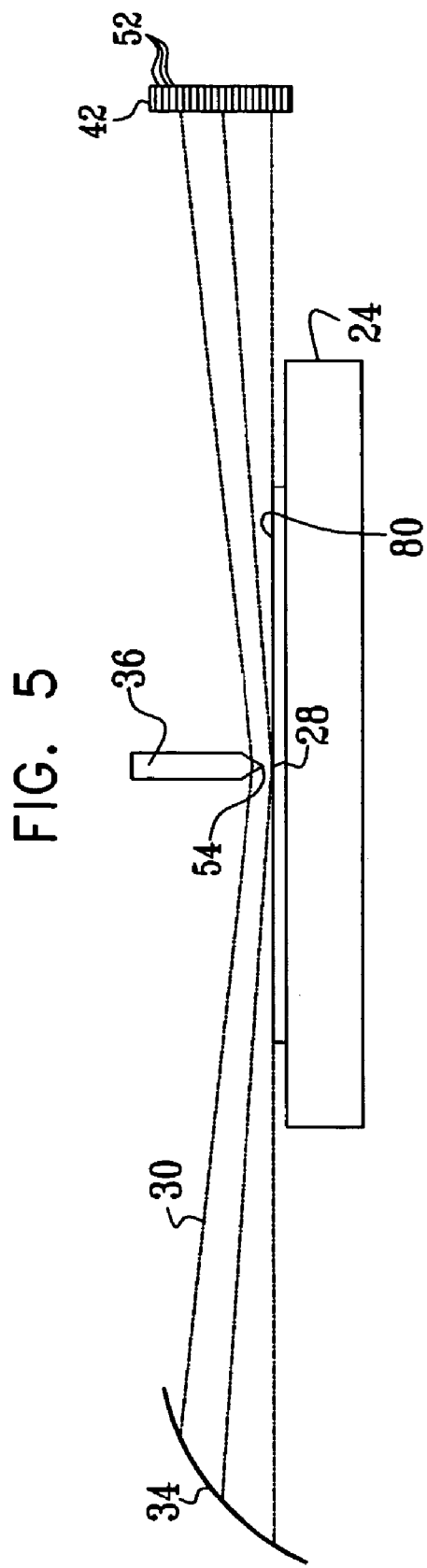

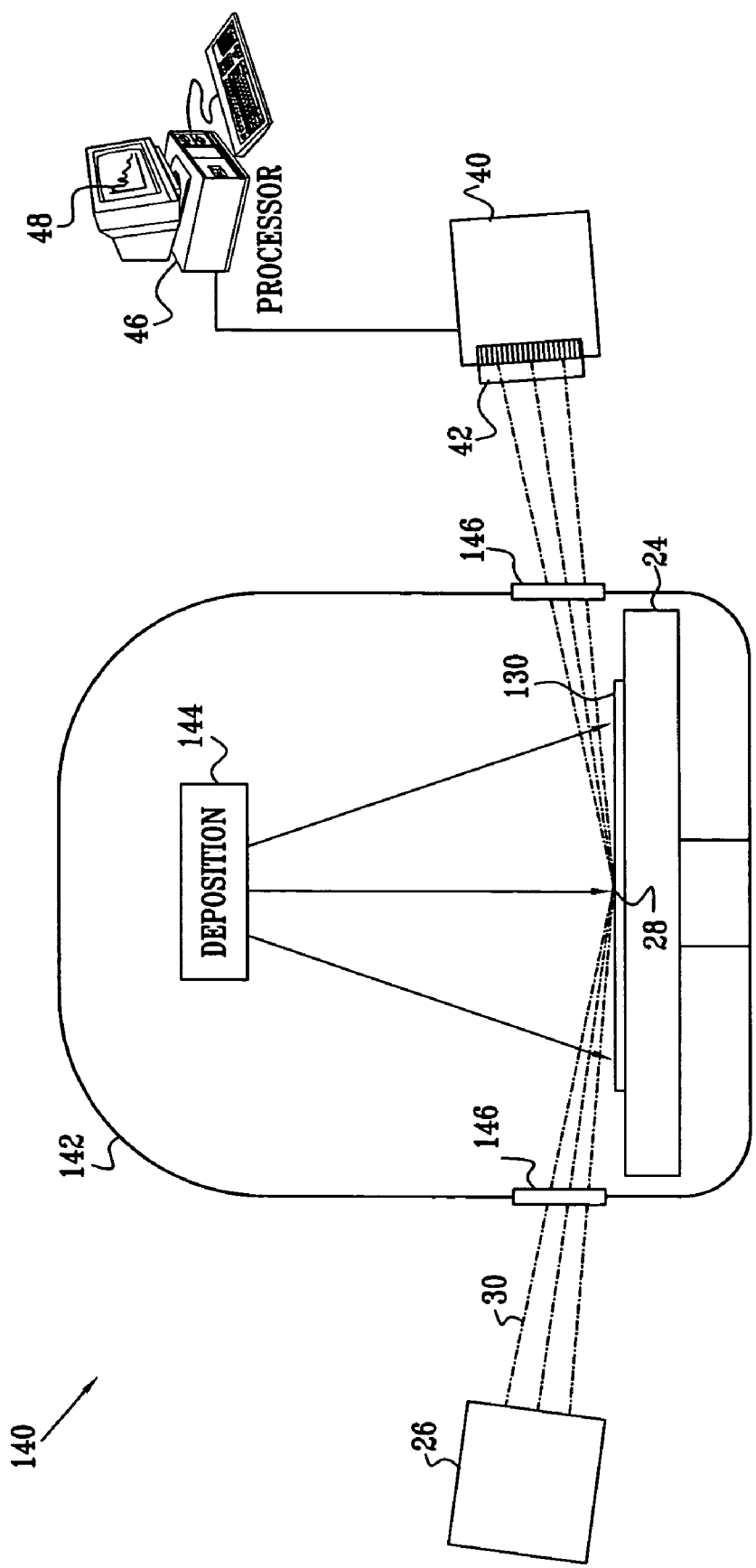

CALIBRATION OF X-RAY REFLECTOMETRY SYSTEM

CROSS-REFERENCE TO RELATED APPLICATIONS

This application is related to U.S. patent application Ser. No. 10/313,280, U.S. patent application Ser. No. 10/364,883, and U.S. patent application Ser. No. 10/689,314, which are assigned to the assignee of the present patent application, and whose disclosures are incorporated herein by reference.

FIELD OF THE INVENTION

The present invention relates generally to analytical instruments, and specifically to instruments and methods for thin film analysis using X-rays.

BACKGROUND OF THE INVENTION

X-ray reflectometry (XRR) is a well-known technique for measuring the thickness, density and surface quality of thin film layers deposited on a substrate. Such reflectometers typically operate by irradiating a sample with a beam of X-rays at grazing incidence, i.e., at a small angle relative to the surface of the sample, in the vicinity of the total external reflection angle of the sample material. Measurement of X-ray intensity reflected from the sample as a function of angle gives a pattern of interference fringes, which is analyzed to determine the properties of the film layers responsible for creating the fringe pattern.

U.S. Pat. No. 5,619,548, to Koppel, whose disclosure is incorporated herein by reference, describes an X-ray thickness gauge based on reflectometric measurement. A curved, reflective X-ray monochromator is used to focus X-rays onto the surface of a sample. A position-sensitive detector, such as a photodiode detector array, senses the X-rays reflected from the surface and produces an intensity signal as a function of reflection angle. The angle-dependent signal is analyzed to determine properties of the structure of a thin film layer on the sample, including thickness, density and surface roughness.

U.S. Pat. Nos. 6,512,814 and 6,639,968, to Yokhin et al., whose disclosures are incorporated herein by reference, describe an X-ray reflectometry system that includes a dynamic shutter, which is adjustably positionable to intercept the X-rays incident on the sample. This shutter, along with other features of the system, permits detection of XRR fringe patterns with high dynamic range. These patents also disclose improved methods for analysis of the XRR fringe pattern in order to determine thin film properties, including density, thickness and surface roughness. The high dynamic range enables the system to determine these properties accurately not only for the upper thin film layer, but also for one or more underlying layers on the surface of the sample.

U.S. Patent Application Publication US 2004/0052330 A1, to Koppel et al., whose disclosure is incorporated herein by reference, describes methods for calibration and alignment of an XRR system for measuring thin films. One such method involves accurately determining, for each sample placement, the pixel number at which the extended plane of the sample intercepts the detector array that is used in the XRR measurements. The incident X-ray intensity corresponding to each pixel is used in making an amplitude calibration of the system. This publication also describes a method for aligning an angle-resolved X-ray reflectometer that uses a focusing optic and validating the focusing optic. In addition, the publication describes methods for correction of measurement errors caused by the tilt or slope of the sample and calibration of the vertical position of the sample.

XRR may also be used in situ, within a deposition furnace, to inspect thin film layers in production on a semiconductor wafer, as described, for example, by Hayashi et al., in U.S. Patent Application Publication US 2001/0043668 A1, whose disclosure is incorporated herein by reference. The furnace is provided with X-ray incidence and extraction windows in its side walls. The substrate upon which the thin film has been deposited is irradiated through the incidence window, and the X-rays reflected from the substrate are sensed through the X-ray extraction window.

SUMMARY OF THE INVENTION

Embodiments of the present invention provide devices and methods for calibration of a system for X-ray spectroscopy, such as an XRR system. In these embodiments, an X-ray source irradiates a sample with a beam of X-rays, which is typically focused to a small spot or line on the surface of the sample. A detector array measures the intensity of the X-rays emitted from the surface as a function of angle. In the case of XRR, the X-rays are emitted by specular reflection from the surface, and each detector element in the array receives X-rays at a different angle of reflection. Thus, the system measures an X-ray spectrum of the sample, but the accuracy of this spectrum may be compromised by imperfect alignment of system components and lack of uniformity in the incident X-ray beam. Precise calibration is needed in order to compensate for these flaws. The embodiments described hereinbelow permit the system to be calibrated with enhanced precision and greater speed than methods known in the art.

In some embodiments of the present invention, an XRR system comprises a beam-limiting optic, such as a knife edge, which is positioned close to the surface of a sample in order to enhance measurement accuracy. For measurements at low incidence angles, the knife edge is lowered very near to the surface, intercepting the incident X-ray beam and thus shortening the lateral dimension of the spot on the surface. Use of the knife edge in this manner improves the spatial resolution (with respect to the surface of the sample) of the XRR measurements, particularly at low angles at which the lateral dimension of the spot is most greatly elongated. Due to non-uniformity in focusing of the X-ray beam onto the surface, however, there are typically non-uniform variations in the beam intensity as a function of angle, which change when the knife edge is inserted into the beam. The non-uniformity tends to reduce the accuracy of measurement of the XRR spectrum of the sample. Methods are provided for measuring and compensating for this non-uniformity and its dependence on the knife position.

In addition, inserting the knife edge into the X-ray beam may shift the location of the focal point of the incident beam (i.e., the location of the center of mass of the focal spot on the surface). In an embodiment of the present invention, this shift in the focal point location is measured. Based on this measurement, the position of the detector array and/or of the knife edge is adjusted when the knife edge is used in order to maintain a constant distance between the focal point and the detector array. The variations in beam uniformity and focal spot position may be mapped in advance as a function of the knife edge, and then used in correcting subsequent measurements made on actual samples.

In another embodiment of the present invention, the orientation of the detector array is adjusted relative to the surface of the sample. For optimal angular resolution, it is desirable that the axis of the array be precisely perpendicular to the sample surface. A method is therefore provided for aligning the array axis based on signals received from the array. Additionally or alternatively, the tilt angle of the sample surface may be measured and, optionally, mapped (as described below), and the known tilt angle may then be used to align the array, as well as the knife edge. Further additionally or alternatively, the measured tilt angle may be used to correct the angular scale of the X-ray spectra captured by the detector array.

In some embodiments of the present invention, the sample comprises a thin, flat structure, such as a semiconductor wafer, which is held on a mounting assembly, such as a chuck or motion stage, during XRR measurement. The mounting assembly shifts the position of the sample relative to the X-ray source and detector so that XRR measurements may be made at multiple different positions on the surface. Typically, the surface angle of the sample in the mounting assembly is not perfectly uniform over the entire surface of the sample. Accurate XRR measurement requires that the tilt angle at each point be known and taken into account. Measuring the surface tilt at all measurement points on the sample surface, however, is time-consuming. To mitigate this problem, the tilt is mapped in advance as a function of position using a reference surface mounted on the mounting assembly. The tilt may be measured using the novel methods described herein or using any other suitable method known in the art. Typically, the measurements are repeated over a number of reference surfaces and then averaged in order to eliminate spurious variations. The tilt map of the reference sample is used to calculate the tilt angles at all measurement points on the sample surface by interpolation.

Although the embodiments described herein are directed primarily to XRR measurement, the principles of the present invention may also be applied in calibration of other radiation-based systems for analysis of materials and thin film measurements.

There is therefore provided, in accordance with an embodiment of the present invention, a method for inspection of a sample, including:

irradiating the sample with a beam of X-rays;

measuring a distribution of the X-rays that are emitted from the sample responsively to the beam, thereby generating an X-ray spectrum;

assessing an effect on the spectrum of a non-uniformity of the beam; and correcting the spectrum responsively to the effect.

In one aspect of the invention, measuring the distribution includes measuring the distribution of the X-rays that are reflected from the sample as a function of an elevation angle relative to a surface of the sample. In disclosed embodiments, irradiating the sample includes focusing the beam so that the X-rays converge on the sample over a range of incidence angles. Typically, focusing the beam includes forming a focal spot on the surface of the sample, and assessing the effect includes assessing a variation in a location of the focal spot. In one embodiment, measuring the distribution of the X-rays includes receiving the reflected X-rays at a detector, and correcting the spectrum includes adjusting a position of the detector responsively to the variation in the location of the focal spot. Adjusting the position may include aligning the detector so as to maintain a constant distance between the focal spot and the detector notwithstanding the variation in the location of the focal spot.

Additionally or alternatively, irradiating the sample includes introducing a beam-limiting optic into the beam, and assessing the effect includes finding the variation in the location due to introduction of the beam-limiting optic. In disclosed embodiments, introducing the beam-limiting optic includes positioning a knife edge so as to intercept the beam in a position adjacent to the focal spot. Typically, positioning the knife edge includes adjusting a position of the knife edge, and finding the variation in the location includes measuring the variation as a function of the position of the knife edge. Additionally or alternatively, adjusting the position includes adjusting a height of the knife edge relative to the surface of the sample, and correcting the spectrum includes determining a correction to apply to the spectrum responsively to the height. Further additionally or alternatively, adjusting the position includes adjusting a lateral position of the knife edge relative to the beam, and wherein correcting the spectrum includes selecting the lateral position so as to minimize the effect of the non-uniformity.

In some embodiments, measuring the distribution of the X-rays includes recording measurement values as a function of the elevation angle, and correcting the spectrum includes modifying the measurement values to account for the variation in the location of the focal spot. In one of these embodiments, assessing the variation includes determining an effective variation in the location of the focal spot as a function of the elevation angle, and modifying the measurement values includes adjusting a mapping of the measurement values to elevation angles responsively to the effective variation.

In disclosed embodiments, irradiating the sample includes introducing a beam-limiting optic into the beam, and assessing the effect includes measuring a variation in the beam as a function of the elevation angle due to introduction of the beam-limiting optic. Typically, irradiating the sample includes directing the beam to impinge on the sample at a focal location, and introducing the beam-limiting optic includes positioning a knife edge so as to intercept the beam in a position adjacent to the focal location. In one embodiment, positioning the knife edge includes adjusting a height of the knife edge relative to the surface of the sample, and correcting the spectrum includes determining a correction to apply to the spectrum responsively to the height. Additionally or alternatively, positioning the knife edge includes adjusting a lateral position of the knife edge relative to the beam, and correcting the spectrum includes selecting the lateral position so as to minimize the effect of the non-uniformity.

In another aspect of the invention, assessing the effect includes determining a correction factor as a function of the elevation angle responsively to the measured variation, and correcting the spectrum includes applying the correction factor to the spectrum. In a disclosed embodiment, determining the correction factor includes directing the beam toward a detector array including a plurality of detector elements, making a first measurement of a flux of the X-rays that is incident on each of the detector elements with the beam-limiting optic in a first position, making a second measurement of the flux of the X-rays that is incident on each of the detector elements with the beam-limiting optic in a second position, and comparing the first and second measurements in order to determine the correction factor.

Typically, measuring the distribution of the X-rays that are reflected from the sample includes measuring the distribution using the detector array with the beam-limiting optic in the first position, and making the first and second measurements includes removing the sample from the beam of X-rays so that the beam is directly incident on the detector array. Additionally or alternatively, making the first and second measurements includes introducing a reflective surface into the beam at a location of the sample so that the X-rays are reflected onto the detector array.

In a further aspect of the invention, irradiating the sample includes introducing a beam-limiting optic into the beam, and assessing the effect includes measuring a variation in the beam due to introduction of the beam-limiting optic. In some embodiments, assessing the effect includes determining a correction vector responsively to the measured variation, and correcting the spectrum includes applying the correction vector to the spectrum. In a disclosed embodiment, determining the correction vector includes directing the beam toward a detector array including a plurality of detector elements, making a first measurement of a flux of the X-rays that is incident on each of the detector elements with the beam-limiting optic in a first position, making a second measurement of the flux of the X-rays that is incident on each of the detector elements with the beam-limiting optic in a second position, and comparing the first and second measurements in order to determine the correction vector. In one embodiment, the detector array has an axis, and the method includes rotating the array so as to position the axis perpendicular to a surface of the sample.

There is also provided, in accordance with an embodiment of the present invention, a method for inspection of a sample, including:

irradiating a surface of the sample with a beam of X-rays;

measuring a distribution of the X-rays that are emitted from the sample responsively to the beam using a detector array, which has an axis and includes a plurality of detector elements arranged along the axis; and rotating the detector array so as to position the axis perpendicular to the surface of the sample.

In disclosed embodiments, measuring the distribution includes measuring the distribution of the X-rays that are reflected from the sample as a function of an elevation angle relative to a surface of the sample. Typically, measuring the distribution of the X-rays includes observing an oscillatory pattern in the X-rays emitted as a function of the elevation angle, and rotating the detector array includes aligning the detector array responsively to the oscillatory pattern. In one embodiment, aligning the detector array includes rotating the detector array so as to maximize a contrast of the oscillatory pattern.

Additionally or alternatively, irradiating the surface includes directing the beam toward the surface at a grazing incidence, and measuring the distribution includes detecting a transition in the distribution corresponding to a plane of the surface of the sample, and rotating the detector array includes aligning the detector array responsively to the transition. Typically, aligning the detector array includes rotating the detector array so as to maximize a sharpness of the transition.

There is additionally provided, in accordance with an embodiment of the present invention, a method for inspection of a sample, including:

providing a tilt map, indicating a characteristic tilt angle of a reference surface at multiple points on the reference surface;

acquiring an X-ray reflectance (XRR) spectrum at a location on a sample;

determining an estimated tilt angle of the location on the sample based on the tilt map; and correcting the XRR spectrum responsively to the estimated tilt angle.

In a disclosed embodiment, providing the tilt map includes measuring the characteristic tilt angle of the reference surface at each of the multiple points. Typically, acquiring the XRR spectrum includes mounting the sample on a mounting assembly, and measuring the characteristic tilt angle includes mounting the reference surface on the mounting assembly, and measuring the characteristic tilt angle while the reference surface is on the mounting assembly. In one embodiment, measuring the characteristic tilt angle includes rotating and translating the mounting assembly, and taking measurements of the tilt angle as a function of rotation and translation.

Additionally or alternatively, determining the estimated tilt angle includes finding the estimated tilt angle by interpolation along a curve in the tilt map.

In disclosed embodiments, the sample includes a semiconductor wafer.

There is further provided, in accordance with an embodiment of the present invention, a method for inspection of a sample, including:

focusing a beam of X-rays onto a focal location on the sample;

positioning a knife edge so as to intercept the beam in a position adjacent to the focal location;

measuring a distribution of the X-rays that are emitted from the sample responsively to the beam and to the position of the knife edge; and adjusting the position of the knife edge responsively to the distribution.

In one aspect of the invention, adjusting the position includes adjusting a lateral location of the knife edge relative to the beam. Typically, measuring the distribution includes measuring a variation in the distribution of the X-rays as a function of a vertical location of the knife edge relative to a surface of the sample at each of a plurality of lateral locations of the knife edge, and adjusting the lateral location includes choosing the lateral location responsively to the variation in the distribution. In a disclosed embodiment, choosing the lateral location includes finding the lateral location that minimizes the variation in the distribution as a function of the vertical location.

Additionally or alternatively, adjusting the position includes adjusting a skew angle of the knife edge relative to a surface of the sample.

There is moreover provided, in accordance with an embodiment of the present invention, a method for inspection of a sample, including:

irradiating the sample with a beam of X-rays over a range of angles of incidence;

positioning a shutter so as to intercept the beam at a predetermined angle;

measuring a distribution of the X-rays that are emitted from the sample responsively to the beam, thereby generating an X-ray spectrum, which includes a shadow of the shutter;

determining a tilt angle of the sample responsively to an angular position of the shadow in the spectrum; and processing the spectrum responsively to the tilt angle.

In one embodiment, measuring the distribution of the X-rays includes measuring the distribution of the X-rays that are reflected from the sample as a function of the elevation angle relative to a surface of the sample, and processing the spectrum includes calibrating the spectrum with respect to the tilt angle. Typically, the predetermined angle is below a critical angle of the sample for total external reflection.

In another embodiment, measuring the distribution includes finding a current angular position of the shadow, and determining the tilt angle includes comparing the current angular position to a reference angular position of the shadow, which is indicative of a zero tilt angle. Typically, comparing the current angular position to the reference angular position includes finding a difference between the current and reference angular positions, and determining the tilt angle of the sample to be equal to half the difference.

There is furthermore provided, in accordance with an embodiment of the present invention, a method for inspection of a sample, including:

focusing a beam of X-rays onto a focal location on the sample;

measuring a distribution of the X-rays that are reflected from the sample responsively to the beam, thereby generating an actual reflectance spectrum;

estimating a spot size of the beam on the sample at the focal location;

computing a simulated reflectance spectrum of the sample responsively to the spot size; and fitting the simulated reflectance spectrum to the actual reflectance spectrum in order to determine one or more properties of the sample.

In one aspect of the invention, computing the simulated reflectance spectrum includes blurring the simulated reflectance spectrum based on an angular spread of the reflected X-rays due to the spot size, as well as due to the detector vertical pixel size and inaccuracy in alignment. In a disclosed embodiment, estimating the spot size includes assessing a variation in an effective spot size of the beam as a function of an elevation angle relative to the sample, and blurring the simulated reflectance spectrum includes applying a variable blur to the simulated reflectance spectrum responsively to the variation in the effective spot size.

In another aspect of the invention, focusing the beam of X-rays includes positioning a beam-limiting optic in the beam, and estimating the spot size includes determining the spot size as a function of a position of the beam-limiting optic relative to a surface of the sample.

In a disclosed embodiment, fitting the simulated reflectance spectrum to the actual reflectance spectrum includes determining at least one of a thickness, a density and a surface quality of a surface layer of the sample.

There is also provided, in accordance with an embodiment of the present invention, apparatus for inspection of a sample, including:

an X-ray source, which is adapted to irradiate the sample with a beam of X-rays;

a detector assembly, which is arranged to measure a distribution of the X-rays that are emitted from the sample responsively to the beam, thereby generating an X-ray spectrum; and a signal processor, which is adapted to assess an effect on the spectrum of a non-uniformity of the beam and to correct the spectrum responsively to the effect.

In some embodiments, the apparatus includes a beam-limiting optic, which is arranged to be introduced into the beam, wherein the signal processor is adapted to assess the variation in the location due to introduction of the beam-limiting optic. The apparatus may also include a positioning assembly, which is adapted to adjust a position of the beam-limiting optic. The detector assembly may include a detector array, which includes a plurality of detector elements.

There is additionally provided, in accordance with an embodiment of the present invention, apparatus for inspection of a sample, including:

an X-ray source, which is adapted to irradiate a surface of the sample with a beam of X-rays;

a detector array, which has an axis and includes a plurality of detector elements arranged along the axis, and which is arranged to measure a distribution of the X-rays that are emitted from the sample responsively to the beam; and an alignment mechanism, which is coupled to rotate the detector array so as to position the axis perpendicular to the surface of the sample.

There is further provided, in accordance with an embodiment of the present invention, apparatus for inspection of a sample, including:

an X-ray source, which is adapted to irradiate a sample with a beam of X-rays;

a detector, which is adapted to receive the X-rays reflected from a location on the sample so as to acquire an X-ray reflectance (XRR) spectrum of the sample at the location; and a signal processor, which is adapted to receive a tilt map, indicating a characteristic tilt angle of a reference surface at multiple points on the reference surface, and to determine an estimated tilt angle of the first location on the sample based on the tilt map, and to correct the XRR spectrum responsively to the estimated tilt angle.

There is moreover provided, in accordance with an embodiment of the present invention, apparatus for inspection of a sample, including:

an X-ray source, which is adapted to focus a beam of X-rays onto a focal location on the sample;

a knife edge;

a positioning assembly, which is adapted to position the knife edge so as to intercept the beam in a position adjacent to the focal location;

a detector assembly, which is arranged to measure a distribution of the X-rays that are emitted from the sample, thereby generating an X-ray spectrum; and a signal processor, which is adapted to receive the X-ray spectrum, and to assess an effect of the position of the knife edge on the X-ray spectrum, and to cause the positioning assembly to adjust the position of the knife edge responsively to the effect.

There is furthermore provided, in accordance with an embodiment of the present invention, apparatus for inspection of a sample, including:

an X-ray source, which is adapted to irradiate the sample with a beam of X-rays over a range of angles of incidence;

a shutter, which is positioned so as to intercept the beam at a predetermined angle;

a detector assembly, which is arranged to measure a distribution of the X-rays that are emitted from the sample responsively to the beam, thereby generating an X-ray spectrum, which includes a shadow of the shutter; and a signal processor, which is adapted to determine a tilt angle of the sample responsively to an angular position of the shadow in the spectrum, and to process the spectrum responsively to the tilt angle.

There is also provided, in accordance with an embodiment of the present invention, apparatus for inspection of a sample, including:

an X-ray source, which is adapted to focus a beam of X-rays onto a focal location on the sample;

a detector assembly, which is adapted to measure a distribution of the X-rays that are reflected from the sample responsively to the beam, thereby generating an actual reflectance spectrum; and a signal processor, which is adapted to estimate a spot size of the beam on the sample at the focal location, to compute a simulated reflectance spectrum of the sample responsively to the spot size, and to fit the simulated reflectance spectrum to the actual reflectance spectrum in order to determine one or more properties of the sample.

There is additionally provided, in accordance with an embodiment of the present invention, a cluster tool for producing microelectronic devices, including:

a deposition station, which is adapted to form a thin-film layer on a surface of a semiconductor wafer; and an inspection station, including:

an X-ray source, which is adapted to irradiate the semiconductor wafer with a beam of X-rays;

a detector assembly, which is arranged to measure a distribution of the X-rays that are emitted from the semiconductor wafer responsively to the beam, thereby generating an X-ray spectrum; and a signal processor, which is adapted to assess an effect on the spectrum of a non-uniformity of the beam and to correct the spectrum responsively to the effect.

There is further provided, in accordance with an embodiment of the present invention, apparatus for producing microelectronic devices, including:

a production chamber, which is adapted to receive a semiconductor wafer;

a deposition device, which is adapted to deposit a thin-film layer on a surface of the semiconductor wafer within the chamber;

an X-ray source, which is adapted to irradiate the semiconductor wafer in the production chamber with a beam of X-rays;

a detector assembly, which is arranged to measure a distribution of the X-rays that are emitted from the semiconductor wafer responsively to the beam, thereby generating an X-ray spectrum; and a signal processor, which is adapted to assess an effect on the spectrum of a non-uniformity of the beam and to correct the spectrum responsively to the effect.

The present invention will be more fully understood from the following detailed description of the embodiments thereof, taken together with the drawings in which:

BRIEF DESCRIPTION OF THE DRAWINGS

FIG. 4B is a schematic plot of an X-ray reflectance spectrum, in accordance with an embodiment of the present invention;

FIG. 5 is a schematic side view of a focused X-ray beam cut by a movable knife edge and reflected from a test surface, in accordance with an embodiment of the present invention;

FIG. 12 is a schematic side view of a semiconductor processing chamber with X-ray inspection capability, in accordance with an embodiment of the present invention.

DETAILED DESCRIPTION OF EMBODIMENTS

Figure 1:
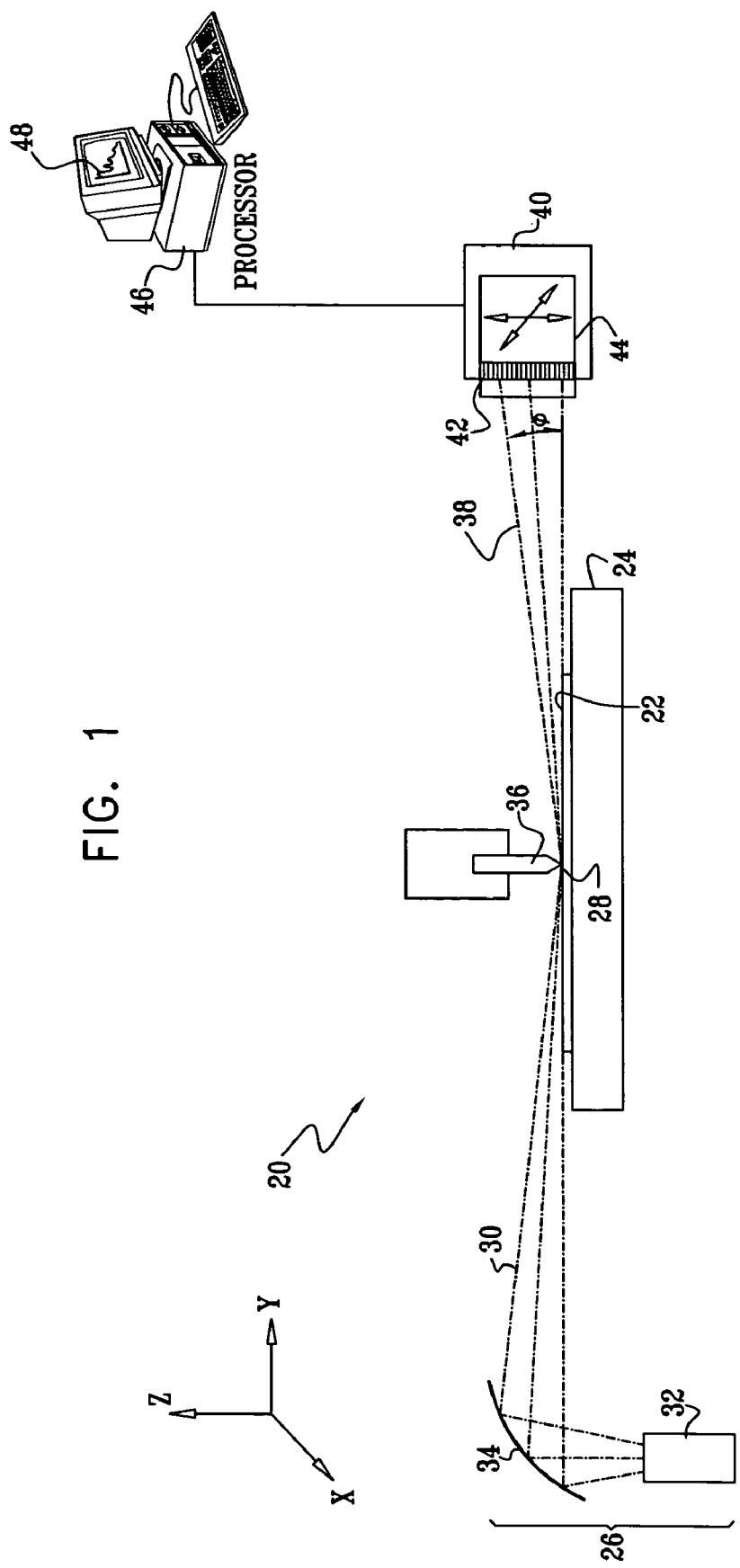
FIG. 1 is a schematic side view of a system for XRR, in accordance with an embodiment of the present invention.

Reference is now made to FIG. 1, which is a schematic side view of a system 20 for X-ray reflectometry (XRR) of a sample 22, in accordance with an embodiment of the present invention. Sample 22 is mounted on a mounting assembly, such as a motion stage 24, allowing accurate adjustment of the position and orientation of the sample. An X-ray source 26 irradiates a small area 28 on sample 22 with a converging beam 30 of X-rays. Typically, source 26 comprises an X-ray tube 32 with monochromatizing optics 34. A number of different types of monochromatizing optics that may be used in system 20 are described in U.S. Pat. No. 6,381,303, whose disclosure is incorporated herein by reference. For example, the optics may comprise a curved crystal monochromator, such as the Doubly-Bent Focusing Crystal Optic, produced by XOS Inc., of Albany, N.Y. Other suitable optics are described in the above-mentioned U.S. Pat. No. 5,619,548. The doubly-curved focusing crystal causes beam 30 to converge in both the horizontal and vertical directions. Alternatively, a cylindrical optic may be used to focus beam 30 so that the beam converges to a line on the sample surface. Further possible optical configurations will be apparent to those skilled in the art.

X-rays are reflected from sample 22 in a diverging beam 38. The reflected X-rays are collected by a detector assembly 40, which comprises a detector array 42, such as a CCD array. Although for simplicity of illustration, only a single row of detectors elements is shown in the figures, with a relatively small number of detector elements, array 42 generally includes a greater number of elements, arranged as either a linear array or a matrix (two-dimensional) array. Detector assembly further comprises an alignment mechanism 44, for adjusting the position and orientation of array 42 relative to sample 22 and to the other components of system 20. Further aspects of detector assembly 40 are described in the above-mentioned U.S. Pat. No. 6,512,814.

A signal processor 46 receives and analyzes the output of assembly 40, so as to determine a distribution 48 of the flux of X-ray photons reflected from sample 22 as a function of angle at a given energy or over a range of energies. Typically, sample 22 has one or more thin surface layers, such as thin films, at area 28. Consequently, distribution 48 as a function of elevation angle exhibits a structure that is characteristic of interference and/or diffraction effects due to the surface layer and interfaces between the layers. Processor 46 analyzes the angular distribution in order to determine characteristics of one or more of the surface layers of the sample, such as the thickness, density, composition and surface quality of the layer, using methods of analysis known in the art. Such methods are described, for example, in the above-mentioned U.S. Pat. No. 6,512,814.

It can be seen in FIG. 1 that because of the low range of angles at which beam 30 is incident on sample 22, typically below 5°, the focal spot of the beam is elongated laterally along the beam axis (i.e., along the Y-axis in FIG. 1). The elongation is particularly pronounced at very low angles, near 0°. Therefore, to enhance the resolution of low-angle measurements, a knife edge 36 is positioned to cut the upper portion of the incident beam. For measurements at low incidence angles, the knife edge is lowered very near to the surface, intercepting the incident X-ray beam and thus shortening the lateral dimension of the spot on the surface. For high-angle measurements, the knife edge may be raised out of the way, to allow the full intensity of the X-ray beam to be used. Such operation of the knife edge allows measurements to be made with high spatial resolution, particularly at low angles at which the lateral dimension of the spot is most greatly elongated, while maintaining high sensitivity even at high angles. Knife edge 36 may be used in conjunction with a dynamic shutter (not shown), as described in the above-mentioned U.S. Pat. No. 6,512,814.

When knife edge 36 is lowered sufficiently, most of incident beam 30 is cut off, and the lateral dimension of the X-ray spot on area 28 is reduced. Typically, the knife edge is lowered to within less than 10 μm of the surface of sample 22, and possibly to as little as 1 μm or less from the surface. The lateral dimension of the spot may thus be reduced to 0.5 mm or less, instead of the typical dimension of 5 mm or more when the knife-edge is not used. A vertical slit (not shown) may also be used to reduce the transverse dimension of the spot on the sample surface. The reduced spot size on the sample means that low-angle reflection measurements made by system 20 have enhanced spatial resolution, providing more detailed information about thin film microstructures on sample 22. Alternatively or additionally, when a certain area of the sample, such as a patterned semiconductor wafer, must be set aside for testing, the small spot size enables a smaller portion of sample "real estate" to be used for this purpose.

Ideally, if incident beam 30 were perfectly uniform, insertion of knife edge 36 into the beam would reduce the intensity of reflected beam 38 (as well as of the direct beam, which strikes array 42 without reflection) uniformly as a function of angle, but would not change the relative angular distribution of the reflected radiation. In practice, however, the incident beam is not uniform, due, for example, to aberrations in optics 34. Therefore, the shape of distribution 48 typically changes depending on the position of knife edge 36. These changes can compromise the accuracy of the thin film measurements that are derived from the XRR spectra. Embodiments of the present invention that are described hereinbelow provide methods for measuring and compensating for the effect of knife edge 36 on the non-uniform beam.

Figure 2A:
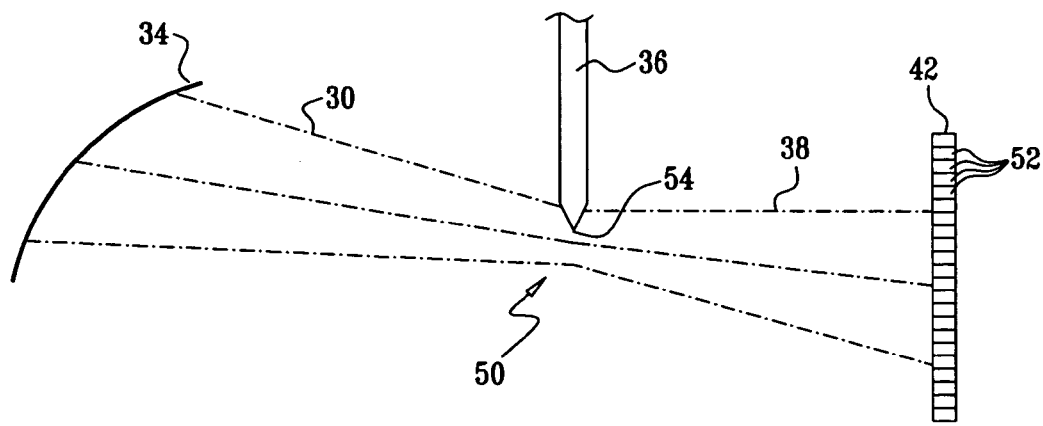
FIGS. 2A and 2B are schematic side views of a focused X-ray beam cut by a movable knife edge, in accordance with an embodiment of the present invention.
Figure 2B:
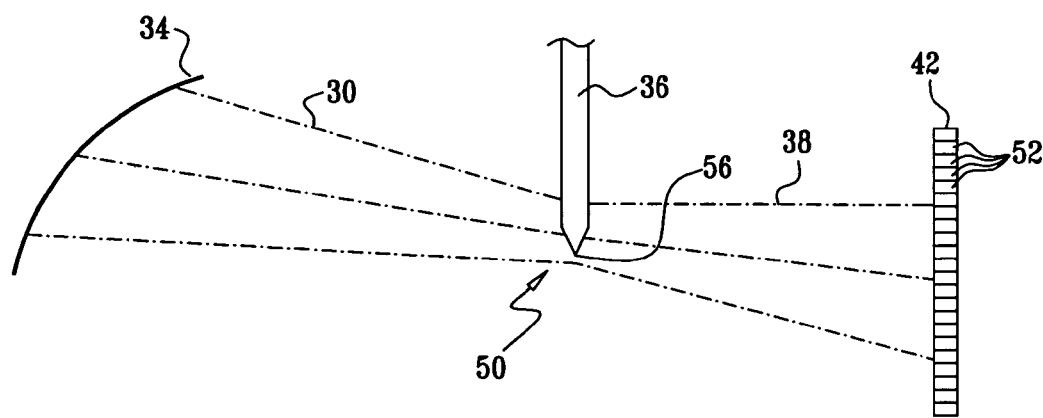

FIGS. 2A and 2B are schematic side views showing beam 30 cut by knife edge 36 in two different positions 54 and 56 during a calibration procedure, in accordance with an embodiment of the present invention. For the purpose of this procedure, sample 22 and stage 24 are removed from the area of beam 30, so that beam 38 strikes detector array 42 directly, without reflection from any intervening surface. Knife edge 36 intercepts beam 30 at a beam waist 50, corresponding to the position of the focus of beam 30 in area 28 on the surface of sample 22 (FIG. 1). In position 54, the lower tip of the knife edge is located at a certain, small distance (for example, 10 μm) above the plane of the sample surface, whereas in position 56, the lower tip of the knife edge is located at the same distance (10 μm) below the surface plane. Signals received by elements 52 of detector array 42 in both positions of the knife edge are conveyed to processor 46 for analysis.

Figure 3:
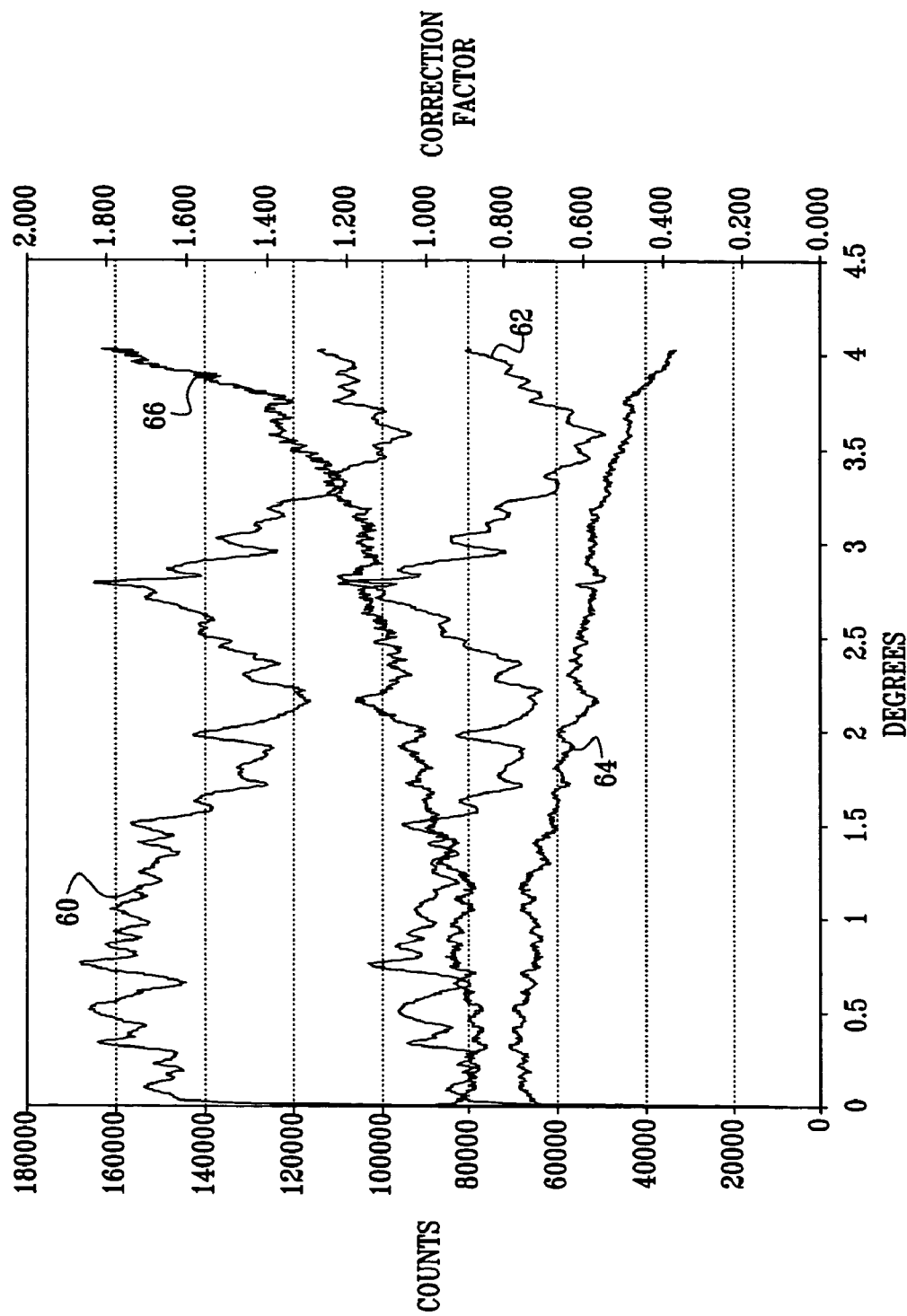
FIG. 3 is a schematic plot of X-ray intensity as a function of angle and of a correction factor derived from the X-ray intensity, in accordance with an embodiment of the present invention.
Figure 4A:
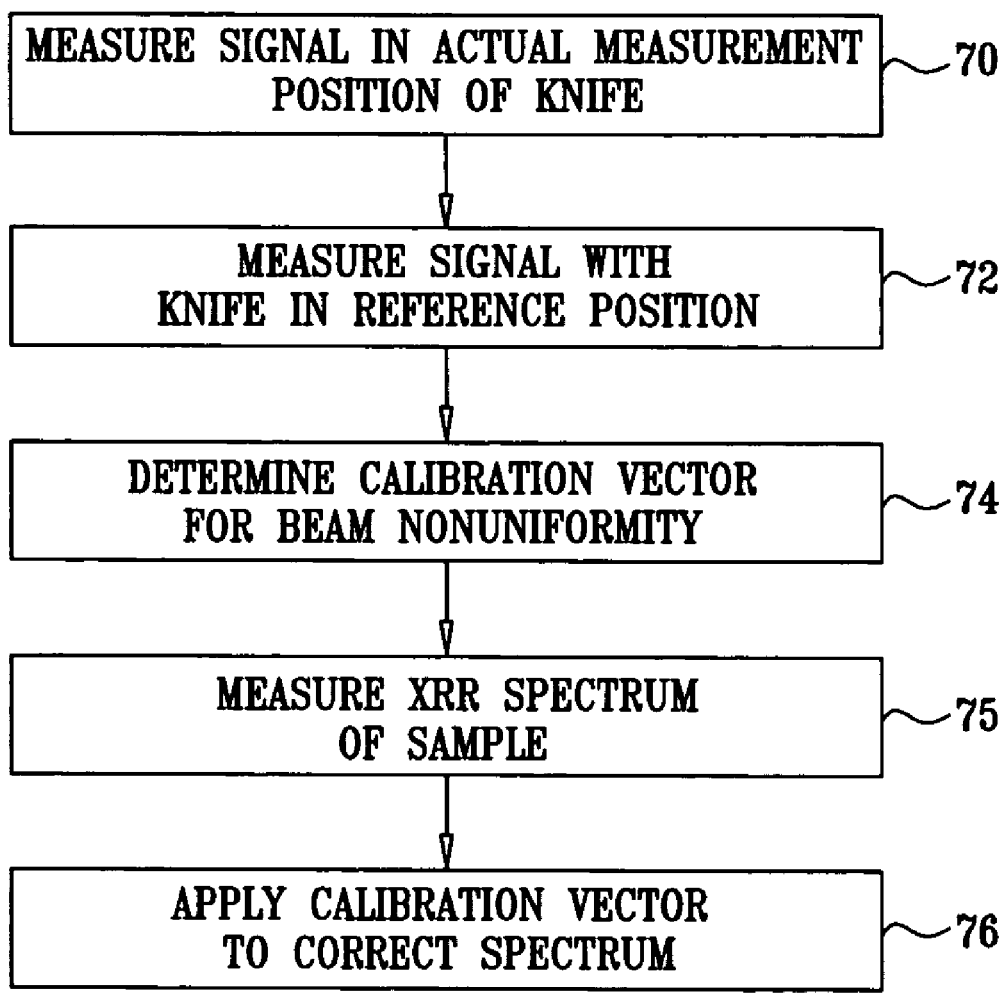
FIG. 4A is a flow chart that schematically illustrates a method for calibration of beam non-uniformities, in accordance with an embodiment of the present invention.

Reference is now made to FIGS. 3 and 4A, which schematically illustrate a procedure for calibration of non-uniformity effects due to knife edge 36, in accordance with an embodiment of the present invention. FIG. 3 is a plot that schematically illustrates simulated results of the measurements made in the configurations of FIGS. 2A and 2B, while FIG. 4A is a flow chart showing the steps in the calibration procedure. The procedure starts with a measurement of X-ray flux by array 42 while knife edge 36 is in its normal position for XRR measurement, such as in position 54 (FIG. 2A), at an actual measurement step 70. A trace 60 in FIG. 3 shows the X-ray flux measured by array 42 with knife edge 36 in this position 54. The results are shown in units of electrons counted per element 52 as a function of elevation angle. The measurement is repeated with the knife edge in a reference position, such as position 56 (FIG. 2B), at a reference measurement step 72. A trace 62 in FIG. 3 shows this reference measurement.

The measurements made at steps 70 and 72 are used in determining a calibration vector, to compensate for the non-uniformity of beam 30, at a calibration step 74. For this purpose, processor 46 calculates the difference between traces 60 and 62 as a function of angle. This difference is illustrated by a trace 64 in FIG. 3. The processor then calculates a correction vector based on the difference indicated by trace 64. The correction vector comprises a scalar correction factor as a function of angle, as shown by a trace 66 in FIG. 3. In the present example, the correction factor is determined by taking the inverse of the difference between traced 60 and 62, and then normalizing so that application of the correction vector does not change the average intensity of the spectrum. Steps 70-74 may be repeated for multiple different heights of knife edge 36 in order to generate a set of correction vectors for the different height settings. Correction vectors for intermediate height settings are determined by interpolation.

Sample 22 is now introduced and aligned in the path of beam 30, with knife edge 36 in position 54, at an XRR measurement step 75. In preparation for or as part of the measurement, the tilt angle and vertical (Z) position of area 28 are determined relative to a known zero reference. Any suitable method may be used for determining the tilt angle and vertical position, such as the methods described hereinbelow or methods described in U.S. patent application Ser. No. 10/689,314, filed Oct. 20, 2003, which is assigned to the assignee of the present patent application, and whose disclosure is incorporated herein by reference, or other methods known in the art. XRR distribution 48 is measured by array 42 as a function of elevation angle. The angular scale of the measurement is corrected for the tilt angle and vertical position of area 28. The measured XRR output of each element 52 of detector array 42 is then multiplied by the corresponding correction factor for the respective angle of reflection measured by the element, at a correction step 76. (Alternatively, the correction vector may be adjusted before multiplication by the tilt angle and vertical position of area 28.) As a result, the XRR spectrum more accurately reflects the actual structure of the surface layers of the sample, while artifacts due to beam non-uniformity are reduced.

FIG. 4B is a schematic plot showing an exemplary XRR spectrum 77 of a sample, in accordance with an embodiment of the present invention. The spectrum shown in FIG. 4B is taken from the above-mentioned U.S. Pat. No. 6,512,814, and details of the steps used in capturing this spectrum are described there. The intensity of the individual signals generated by elements 52 of array 42 are corrected as described above at step 76. The resulting spectrum 77 contains a fringe pattern of peaks 78 and intervening troughs 79 whose characteristics are indicative of the surface structure of sample 22. Further aspects of the analysis of this fringe pattern are described hereinbelow.

FIG. 5 shows another method for calibrating the non-uniformity of incident beam 30, in accordance with an alternative embodiment of the present invention. For the purposes of this method, a reflective reference sample 80 is placed on stage 24 in place of the actual test sample. Typically, sample 80 comprises A polished metal surface. Array 42 measures X-ray reflection from the surface of sample 80 with knife edge 36 in actual measurement position 54 at step 70 (FIG. 4A). The measurement is repeated with knife edge 36 in a reference position away from the surface of the sample, so that the knife edge does not intercept beam 30, at step 72. To determine the calibration vector at step 74, processor 46 divides the X-ray flux measured by each element 52 with knife edge 36 in the reference position by the flux measured with the knife edge in position 54. This calibration vector is then applied to actual XRR spectra of sample 22 at step 76.

The use of knife edge 36 to intercept beam 30 may also shift the location of the focal point of beam 30 in area 28, relative to the focal point when the knife edge is removed from the beam. In this context, since the focal spot typically extends over a length of one to several millimeters on the surface of sample 22, the focal point is defined by the location of the center of mass of the distribution of X-ray radiation on the surface. The respective elevation angle $\phi$ (FIG. 1) that corresponds to each element 52 of detector array 42 is given by arctan(h/d), wherein h is the height of the element above the sample plane, and d is the distance from the focal point to the detector array. Accurate analysis of the XRR spectra requires that the elevation angles be known very precisely. Movement of the focal point of beam 30 due to the use of knife edge 36 can change the distance between the focal point and the detector array, and may thus compromise the accuracy of XRR measurements.

In order to overcome this problem, the shift in focal point location is measured as a function of the position of knife edge 36. One method that can be used to measure the focal point location is to place a reference sample of known characteristics on stage 24, in place of sample 80 in FIG. 5, and measure the XRR spectrum of the sample. If the reference sample has a thin film surface layer of known thickness, then the XRR spectrum will comprise a pattern of fringes with known angular spacing, as shown above in FIG. 4B. Since the angular spacing of the fringes is constant, the fringe spacing in spectrum 77 is expected to be identical for all positions of knife edge 36 as long as there is no variation in the focal point location. In practice, the focal point location shifts with knife edge position due to non-uniformity of beam 30, and the fringe spacing changes accordingly due to the variation in the distance between the focal point and detector array 42.

Thus, the dependence of focal point location on the knife edge position may be determined by measuring the changes in fringe spacing for different positions of the knife edge. Alignment mechanism 44 in detector assembly 40 is then used to adjust the lateral position of array 42 (i.e., to shift the entire array forward or back along the Y-direction) based on this measurement, so that the distance from the focal point to the array remains constant regardless of the position of knife edge 36. Alternatively, array 42 may be held stationary, and the mapping of detector elements 52 to elevation angle $\phi$ may be adjusted to account for the varying distance d. The measurement and calculation of adjustment factors may be performed in advance for different settings of the height of knife edge 36, and then applied in actual measurements depending on the actual position of the knife edge.

Alternatively or additionally, the lateral (Y-direction) location of knife edge 36 may be adjusted in order to minimize the variation in focal point location with the height (Z-axis position) of the knife edge. If converging beam 30 were ideally focused to waist 50 (FIG. 2A), and knife edge 36 were positioned precisely at the waist, then the focal point location of the beam would not change with variation of the height of the knife edge. Displacement of the knife edge in the Y-direction from the waist location, however, causes the focal point location to shift with knife height. In order to minimize this variation, the variation in focal point location with knife height may be measured at a number of different positions of the knife edge along the Y-direction. The Y-position of the knife edge is then set at the location that minimizes the focal point shift.

Alternatively or additionally, other methods may be used to measure and correct for beam non-uniformities introduced by the use of knife edge 36. All such methods are considered to be within the scope of the present invention. For example, it is also possible to measure the location of the center of mass of the X-ray focal spot in area 28 separately for different reflection angles (and hence for different elements 52 of array 42). In one embodiment, this measurement is performed by observing the relative variation in the X-ray intensity measured by each element 52 as a function of variations in the position of knife edge 36. It is thus possible to find and correct for the variation in focal point position as a function of the angle, as well as of the height of the knife edge. The measured variations in X-ray intensity as a function of knife edge position may also be used to determine the effective focal spot size as a function of reflection angle. In this case, a non-linear correction may be applied to the mapping of detector elements 52 to elevation angle $\phi$.

The focal spot size of X-ray beam in area 28 is also significant in the angular resolution of the spectrum. If the beam could be focused to a precise point, each element 52 of array 42 would receive X-rays reflected from sample 22 in its own, unique angular range, determined only by the height of the detector element and its distance from the focal spot. Because the focal spot spreads over a certain area, however, each element 52 receives X-rays over a larger angular range, which partially overlaps the angular ranges of the neighboring elements. As a result, a certain amount of blur is introduced into spectrum 77 (FIG. 4B). For example, the blur can be estimated as follows:

Blur[deg]=(Effective vertical spot size+Detector element height)/(detector pitch)*Angle step;

Here the angle step is the angular distance (in degrees) between two adjacent elements 52, and the effective vertical spot size is equal to twice the height of knife edge 36 above the surface of sample 22.

Alternatively, other measures of the spot size and the resulting blur may be used. For example, instead of assuming a constant effective vertical spot size in the above formula, a variable measure of the spot size as a function of reflection angle may be used, giving a resulting variation in the estimated blur at different reflection angles. Methods for measuring the effective spot size as a function of angle are described above.

The above-mentioned U.S. Pat. No. 6,512,814 describes a method for parametric modeling of XRR spectra in order to determine properties of thin film layers on sample 22 (such as the layer thickness, density and surface roughness). These properties are determined by fitting simulated spectra calculated by the parametric model to the actual spectra captured by system 20. In an embodiment of the present invention, in order to optimize the accuracy of the fit, the simulated spectrum is blurred by convolution with a blur function, and it is the blurred spectrum that is fitted to the actual spectrum in order to determine the thin film properties. The extent of the convolution kernel is given by the height of knife edge 36, in accordance with the above formula.

Figure 6A:
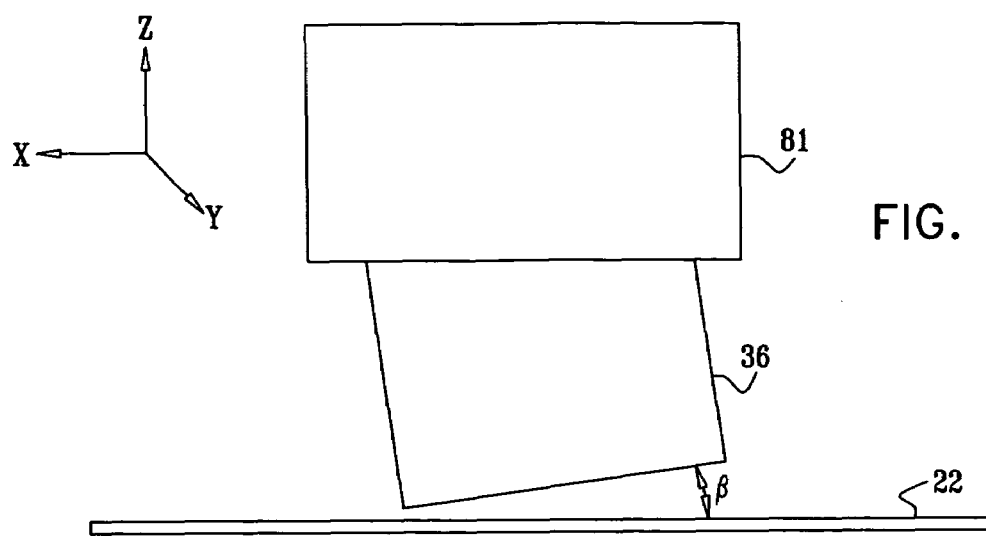
FIG. 6A is a schematic frontal view of a movable knife edge that is used to cut an X-ray beam, in accordance with an embodiment of the present invention.
Figure 6B:
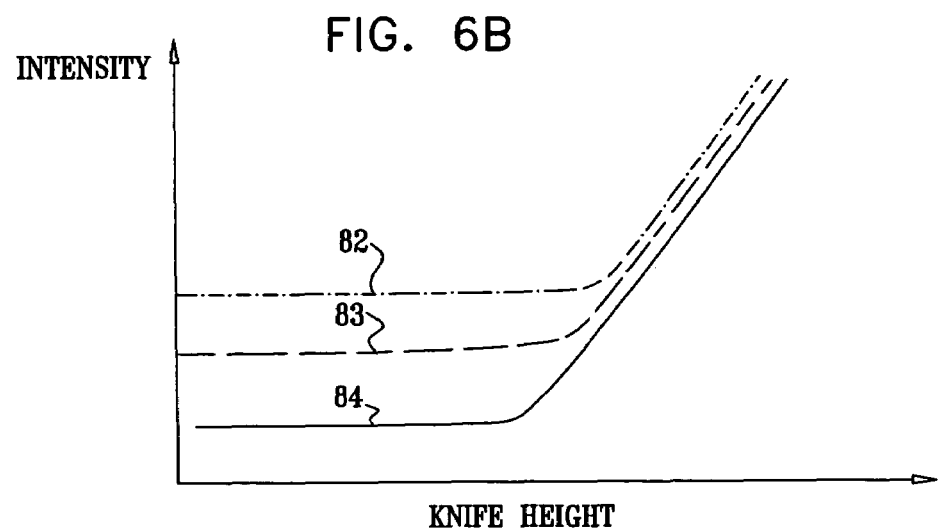
FIG. 6B is a schematic plot of X-ray intensity measured by a detector array as a function of the position of a knife edge that is used to cut the X-ray beam, in accordance with an embodiment of the present invention.

Reference is now made to FIGS. 6A and 6B, which schematically illustrate a method for aligning knife edge 36, in accordance with an embodiment of the present invention. FIG. 6A is a schematic frontal view of knife edge 36 together with a positioning assembly 81 that is used in controlling the position and orientation of the knife edge. Typically, signal processor 46 (FIG. 1) controls assembly 81 based on measurements made by detector assembly 40, as described hereinbelow. The skew angle β of the knife edge is exaggerated in the figure for visual clarity. FIG. 6B is a plot of measurements of X-ray intensity measured in system 20 as a function of the height (Z-axis position) of the knife edge. The measurements are presented at three different settings of the skew angle β, giving three different curves 82, 83 and 84.

If knife edge 36 were precisely parallel to the surface of sample 22, then the X-ray intensity would drop to zero at zero height. In practice, there is almost always a small amount of tilt or other residual imperfection that permits some radiation to pass between the knife edge and the sample surface. The skew angle of the knife edge is adjusted, using positioning assembly 81, in order to minimize the amount of radiation passing through to the detector array at zero height. In this example, the skew would be set to the value that generated curve 84. Furthermore, curves 82, 83 and/or 84 may be extrapolated down to zero intensity in order to calibrate the zero point of the knife height scale. Assembly 81 may also be used in adjusting the height and the Y-displacement of knife edge 36, as described above.

Figure 7:
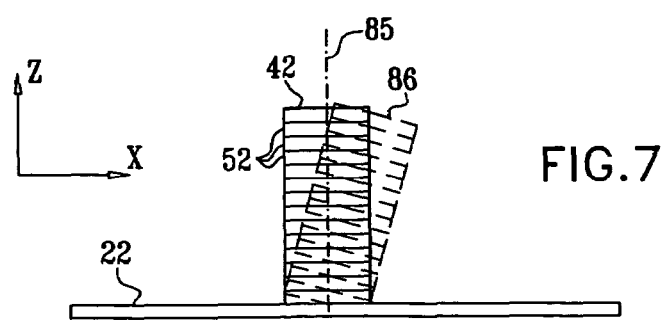
FIG. 7 is a schematic frontal view of a sample and a detector array for receiving X-rays reflected from the sample, illustrating a method for alignment of the detector array, in accordance with an embodiment of the present invention.

FIG. 7 is a schematic frontal view of detector array 42, illustrating another aspect of the calibration of system 20, in accordance with an embodiment of the present invention. Ideally, for optimal angular resolution and accuracy, array 42 is aligned so that an axis 84 of the array is perpendicular to the surface of sample 22. In practice, however, the sample surface may tilt, or the array itself may become misaligned. The result of this sort of tilt or other misalignment is shown in the form of a "shadow array" 86 in FIG. 7. The tilt of array 86 is exaggerated for clarity of illustration.

Figure 8:
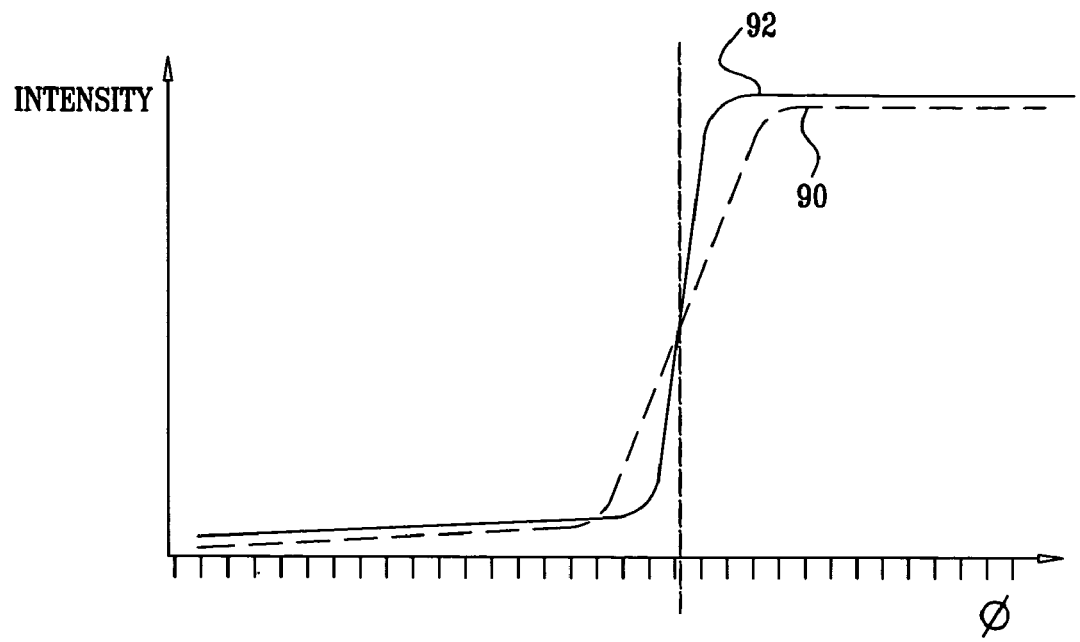
FIG. 8 is a schematic plot of X-ray intensity measured by a detector array in two different orientations, in accordance with an embodiment of the present invention.

FIG. 8 is a schematic plot of X-ray intensity as a function of angle φ, which illustrates a method for aligning array 42 relative to sample 22, in accordance with an embodiment of the present invention. The angle is measured along axis 84 of array 42. To generate plots of this sort, the sample is irradiated with an incident beam at a grazing angle, i.e., roughly parallel to the surface of the sample. As a result, the X-ray flux measured by elements 52 of array 42 that are above the plane of the surface is high, while that measured by the elements below the plane is low. This result is shown in FIG. 8, wherein the dashed vertical line in the figure corresponds to the location of the surface plane of sample 22. The X-ray intensity measured by elements 52 above the surface plane appears to the right of this vertical line, while the intensity measured by the elements below the surface plane appears to the left.

A trace 90 in FIG. 8 corresponds to the intensity measured by "array" 86, while a trace 92 corresponds to the intensity measured when array 42 is properly aligned, with axis 84 perpendicular to the sample surface plane. Trace 92 is characterized by a sharp transition from low to high intensity at the surface plane. In trace 90, however, the transition is more gradual, since elements 52 near the surface plane are partly exposed to the incident X-rays and partly obscured by sample 22. In order to align array 42 so that axis 84 is precisely perpendicular to the sample surface plane, alignment mechanism 44 is operated to rotate the array while processor 46 monitors the sharpness of the transition from low to high flux in the intensity trace of FIG. 8. The angular orientation of array 42 is fixed at the angle that gives the sharpest transition.

Alternatively, other criteria may be used to determine the optimal orientation of axis 84 of array 42. For example, when axis 84 is properly aligned perpendicular to the surface of sample 22, the fringe pattern in the XRR spectrum of the sample will have the greatest contrast, i.e., the difference between the intensities of the peaks of the fringes relative to the troughs between the fringes is maximized. As axis 84 is tilted, this contrast gradually decreases, for the same reason as the transition in trace 92 is sharper than that in trace 90. Therefore, array 42 may be aligned by observing the XRR fringe pattern while rotating axis 84, and choosing the rotation angle that gives the fringes of highest contrast.

Figure 9:
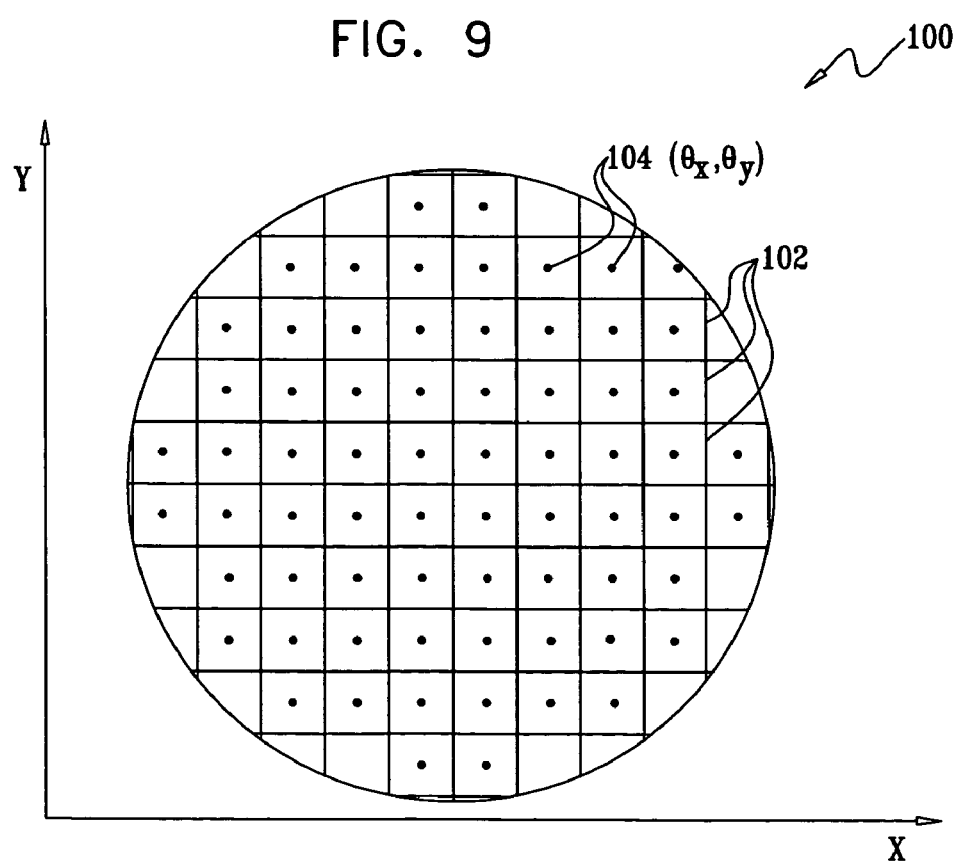
FIG. 9 is a schematic representation of a tilt map, in accordance with an embodiment of the present invention.

FIG. 9 is a schematic representation of a tilt map 100, in accordance with an embodiment of the present invention. As noted earlier, stage 24 shifts sample 22 in the X-Y plane to enable system 20 to measure XRR spectra at multiple locations on the surface of the sample. The surface tilt angle of the sample (i.e., the angle of deviation between a plane that is locally tangent to the surface and the reference X-Y plane) on stage 24 may not be perfectly uniform over the entire surface of the sample. For example, in a typical application of system 20, sample 22 is a semiconductor wafer, which is held in place on stage 24 by suction exerted through vacuum ports (not shown) in the surface of the stage. Under these circumstances, the wafer conforms to the shape of the stage, with deformations due to the force of the suction. As a result, the local tilt angle of the wafer may vary from point to point on the wafer surface. Accurate XRR measurement, however, requires that the tilt angle at each point be known and taken into account.

Tilt map 100 is generated and used in order to facilitate compensation for these tilt angle variations. To produce the map, a reference sample is loaded onto stage 24. The surface of the sample is divided into regions 102, and the surface tilt is measured in each region to give a tilt value 104. The tilt value is typically expressed in terms of tilt angles of the surface about the X- and Y-axes, identified in the figure as $\theta_X$ and $\theta_Y$. Any suitable method that is known in the art may be used to determine the surface tilt. For example, the zero-angle of the surface may be determined in system 20 by means of X-ray measurement techniques, such as the techniques described in the above-mentioned U.S. patent applications Ser. Nos. 10/313,280, 10/364,883, and 10/689,314, or in U.S. Pat. No. 6,680,996, which is also incorporated herein by reference. Another method for measuring tilt using X-rays is described hereinbelow with reference to FIGS. 10A and 10B. Alternatively, optical techniques may be used to determine the surface tilt, such as the technique described in the abovementioned U.S. Patent Application Publication US 2004/0052330 A1.

Generating tilt map 100 with a dense grid of regions 102 is time-consuming, but it need be performed only once, typically by measuring the tilt over the surfaces of a number of reference samples, and then averaging the results. Subsequently, the tilt measurements may be repeated from time to time (at some or all of regions 102 in the tilt map), and the tilt map may be updated accordingly. The tilt angles of other locations on sample 22 are determined by interpolation, based on the measurements and on the tilt characteristics given by map 100. For example, a spline curve or curved surface may be fitted to map 100, and the tilt angle at any desired location on sample 22 may then be found by interpolating along the curve or surface, using the small number of points at which the tilt was actually measured as reference points.

In some embodiments, stage 24 is capable of both X-Y translational movement and rotation about the Z-axis. (The rotation angle is referred to hereinbelow as $\theta_Z$.) Thus, a complete tilt map for a system using such a stage will take into account not only the X-Y grid shown in FIG. 9, but also the rotation angle. The most precise method for X-Y-$\theta_Z$ mapping is to map the entire X-Y grid at multiple different rotation angles. Alternatively, a less time-consuming option would be to make a single two-dimensional map (such as an X-Y map), and then make a further measurement of the effect of movement in the third dimension (for example, measuring the tilt as a function of $\theta_Z$ at one or a few points in the X-Y plane). A further option would be to simply map the tilt as a separate function of movement in the X, Y and $\theta_Z$ directions. Furthermore, the tilt measurements and interpolation may be performed separately for tilt about each of the X- and Y-axes, or alternatively, combined X/Y tilt values may be used. Other methods of measurement and interpolation will be apparent to those skilled in the art.

The interpolated tilt values are then applied in order to correct the XRR results. Typically, the angular scale of each distribution 48 is adjusted to account for the local tilt at the point at which the distribution was measured. Alternatively, the tilt angle of stage 24 or the positions of X-ray source 26 and detector array 42 may be adjusted to compensate for the local tilt. Similarly, the position and orientation of knife edge 36 may be adjusted based on the tilt map so that the knife edge is parallel to the surface of sample 22 at the proper height. When a shutter is used to cut off low-angle radiation (as shown below in FIG. 10A), the shutter angle and height may be similarly adjusted. Other parameters that are used in analyzing the XRR spectrum, such as the beam blur, focal distance of the detector, and the calibration vector, may also be adjusted based on the tilt map.

Figure 10A:
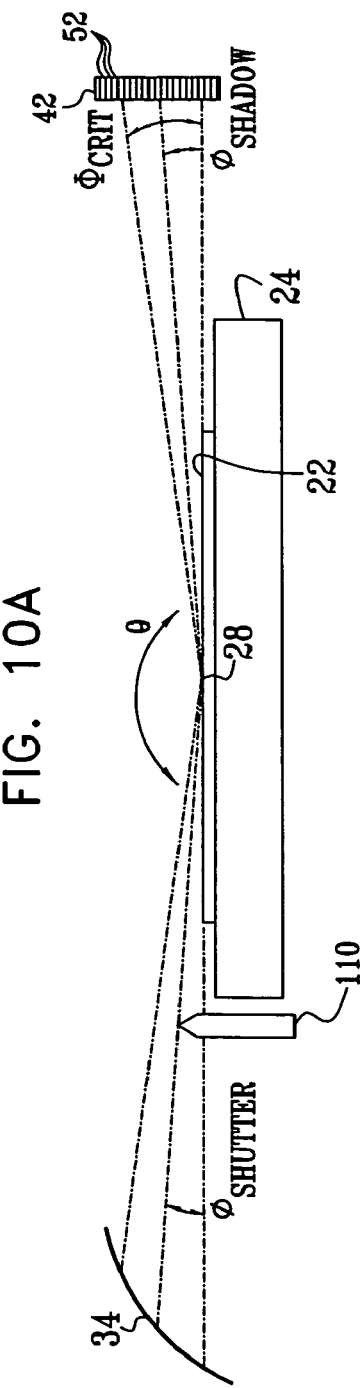
FIG. 10A is a schematic side view of a system for XRR, showing elements of the system that are used in measuring the tilt angle of a sample, in accordance with an embodiment of the present invention.

FIG. 10A is a schematic side view showing elements of system 20 used in a method for measuring tilt of sample 22, in accordance with an embodiment of the present invention. In this embodiment, detector array 42 is used to measure the component of the tilt of area 28 in the $\theta$ direction, i.e., about the X-axis (FIG. 1). For this purpose, a shutter 110 is introduced into the incident converging X-ray beam. The height of shutter 110 is chosen so that the shutter cuts off the incident radiation below a selected angle $\phi_{SHUTTER}$. As a result the shutter casts a shadow on array 42 at a corresponding angle $\phi_{SHADOW}$ and below. (For specular reflection, in the sample tilt angle $\theta=0$, then $\phi_{SHUTTER}=\phi_{SHADOW}$.) Typically, $\phi_{SHUTTER}$ is chosen to be less than the critical angle of sample 22 for total external reflection, $\Phi_{CRIT}$. For example, assuming sample 22 to comprise a silicon wafer, with $\Phi_{CRIT}=0.227°$ at 8.05 keV (CuKα1), $\phi_{SHUTTER}$ may be set to about 0.1°.

Figure 10B:
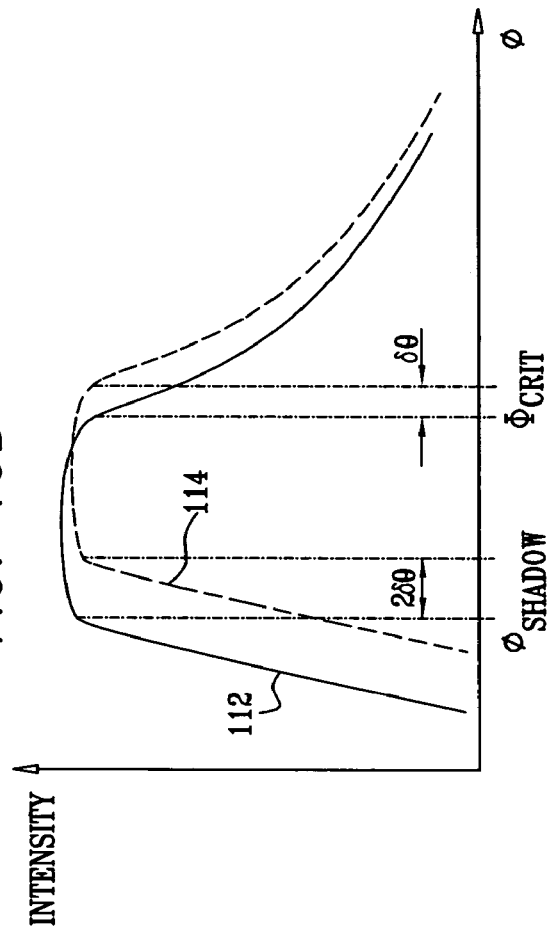
FIG. 10B is a schematic plot of the intensity of X-rays reflected from a sample as a function of elevation angle for two different tilt angles of the sample, in accordance with an embodiment of the present invention.

FIG. 10B is a schematic plot showing reflected X-ray intensity from sample 22 as a function of elevation angle $\phi$, as measured by array 42 in the configuration of FIG. 10A, in accordance with an embodiment of the present invention. Two curves are shown in FIG. 10B:

A reference curve 112, which is measured with sample 22 held in a reference orientation, typically with tilt $\theta=0$; and An uncorrected curve 114, which is measured with sample 22 tilted by a small angle $\delta\theta$.

Curve 112 is characterized by a left shoulder at angle $\phi_{SHADOW}$, marking the upper edge of the shadow cast by shutter 110, and by a right shoulder at angle $\Phi_{CRIT}$, above which the XRR spectrum falls off sharply, as is known in the art. Curve 114 is similar in shape to curve 112, except that the XRR spectrum received from the tilted sample is shifted by the amount of the tilt angle $\delta\theta$. Thus, as shown in FIG. 10B, the right shoulder of curve 114 is shifted by $\delta\theta$ relative to curve 112. On the other hand, by the principles of specular reflection, the point at which shutter 110 is reflected onto array 42 shifts by $2\delta\theta$ when sample 22 is tilted relative to the reference position. Therefore, as shown in FIG. 10B, the left shoulder of curve 114 is shifted by $2\delta\theta$ relative to curve 112.

The characteristics of the curves shown in FIG. 10B may be used in measuring and correcting for the tilt angles of different samples that are used in system 20. Although the right shoulders of curves 112 and 114 are displaced by the tilt angle $\delta\theta$, this relation will hold only as long as curves 112 and 114 are generated using the same sample (or at least samples of the same material). On the other hand, the relative displacement of the left shoulders is a geometrical effect, independent of the sample materials. Thus, the tilt angle $\theta$ of substantially any flat sample may be determined, relative to the known reference orientation at which curve 112 is recorded, using the formula:

$$\theta=\theta_{REF}+\tfrac{1}{2}[\text{current shadow angle}-\text{reference shadow angle}]$$

wherein the shadow angle is determined, for example, by the location of the left shoulder in the XRR curves in question. This approach permits the tilt angle of sample 22 to be determined simply and accurately for each area on the sample that is inspected by XRR with no more than minimal added measurement and computation.

When shutter 110 is used in system 20, it is important that the shutter be precisely parallel to the surface of sample 22 along the X-direction. As noted above, the shutter angle may be adjusted on the basis of the tilt map, which is shown in FIG. 9. Additionally or alternatively, the shutter may be adjusted so as to maximize the sharpness of the shadow of the shutter, as seen in curves 112 and 114. Alternatively, if it is not possible or desirable to adjust the shutter (as well as knife edge 36) to exactly parallel the surface of sample 22 at all positions and orientations of the sample, the effects of the known tilt of the shutter (and/or knife edge) relative to the surface may be taken into account in modeling the XRR spectrum, as described above. These effects may include, for example, blur of the X-ray beam and variations in the effective distance between the focal spot on sample 22 and the elements of array 42.

Figure 11:
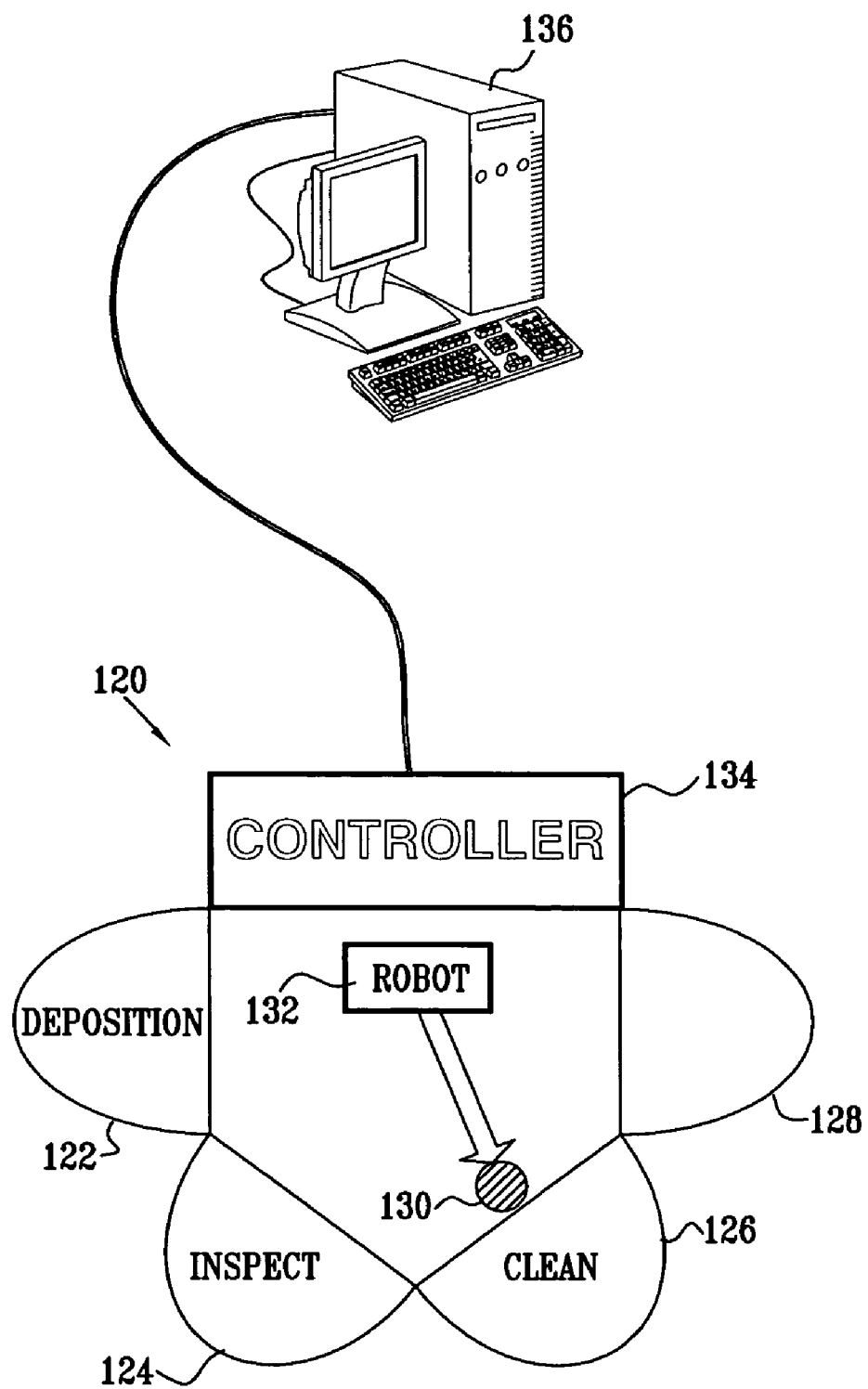
FIG. 11 is a schematic top view of a cluster tool for semiconductor device fabrication, including an inspection station in accordance with an embodiment of the present invention.

FIG. 11 is a schematic top view of a cluster tool 120 for use in semiconductor device fabrication, in accordance with an embodiment of the present invention. The cluster tool comprises multiple stations, including a deposition station 122, for depositing thin films on a semiconductor wafer 130, an inspection station 124, and other stations 126, 128, as are known in the art, such as a cleaning station. Inspection station 124 is constructed and operates in a manner similar to system 20, as described hereinabove. A robot 132 transfers wafer 130 among stations 122, 124, 126, . . . , under the control of a system controller 134. Operation of tool 120 may be controlled and monitored by an operator using a workstation 136, coupled to controller 134.

Inspection station 124 is used to perform X-ray inspection of wafers by XRR. Such inspection is typically carried out before and/or after selected steps in production processes carried out by deposition station 122 and other stations in tool 120. The inspection station is calibrated using the methods described above. Use of station 124 allows early detection of process deviations and convenient adjustment and evaluation of process parameters on production wafers, using controller 134 and possibly workstation 136.

FIG. 12 is a schematic side view of a system 140 for semiconductor wafer fabrication and in situ inspection, in accordance with another embodiment of the present invention. System 140 comprises a vacuum chamber 142, containing deposition apparatus 144, for creating thin films on wafer 130, as is known in the art. The wafer is mounted on motion stage 24 within chamber 142. The chamber typically comprises X-ray windows 146, which may be of the type described in the above-mentioned Patent Application Publication US 2001/0043668 A1. X-ray source 26 irradiates area 28 on wafer 130 via one of windows 146, in the manner described above. Some of the elements shown in FIG. 1 are omitted from FIG. 10 for the sake of simplicity, but typically, elements of this sort are integrated into system 140, as well.

X-rays reflected or diffracted from area 28 are received by array 42 in detector assembly 40 via another one of windows 146. Processor 46 receives signals from detector assembly 40, and processes the signals in order to assess characteristics of thin-film layers in production within chamber 142, by measuring the XRR spectrum of wafer 130. The elements of system 140 that are used in the XRR measurement are calibrated in the manner described above. The results of the XRR assessment may be used in controlling deposition apparatus 144 so that the films produced by system 140 have desired characteristics, such as thickness, density, composition and surface roughness.

Although the embodiments described above refer specifically to X-ray reflectometry, the principles of the present invention may similarly be used, mutatis mutandis, in other fields of X-ray analysis. Exemplary fields of application include X-ray fluorescence (XRF) analysis, including particularly grazing emission XRF, as well as other XRF techniques known in the art. Grazing emission XRF is described, for example, in an article by Wiener et al., entitled "Characterization of Titanium Nitride Layers by Grazing-Emission X-ray Fluorescence Spectrometry," in *Applied Surface Science* 125 (1998), p. 129, which is incorporated herein by reference. X-ray fluorescence measurement may be incorporated in system 20, as described in the above-mentioned U.S. Pat. No. 6,381,303, for example. Additionally or alternatively, the system may be adapted to make small-angle scattering measurements, as described in the above-mentioned U.S. patent application Ser. No. 10/364,883, or X-ray diffraction measurements. Furthermore, the principles of system 20 may be implemented in position-sensitive detection systems for other energy ranges, such as for detection of gamma rays and other nuclear radiation.

It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. A method for inspection of a sample, comprising:
   irradiating the sample with a beam of X-rays;
   measuring a distribution of the X-rays that are emitted from the sample responsively to the beam, thereby generating an X-ray spectrum;
   assessing an effect on the spectrum of a non-uniformity of the beam; and
   correcting the spectrum responsively to the effect.

2. The method according to claim 1, wherein measuring the distribution comprises measuring the distribution of the X-rays that are reflected from the sample as a function of an elevation angle relative to a surface of the sample.

3. The method according to claim 2, wherein irradiating the sample comprises focusing the beam so that the X-rays converge on the sample over a range of incidence angles.

4. The method according to claim 3, wherein focusing the beam comprises forming a focal spot on the surface of the sample, and wherein assessing the effect comprises assessing a variation in a location of the focal spot.

5. The method according to claim 4, wherein measuring the distribution of the X-rays comprises receiving the reflected X-rays at a detector, and wherein correcting the spectrum comprises adjusting a position of the detector responsively to the variation in the location of the focal spot.

6. The method according to claim 5, wherein adjusting the position comprises aligning the detector so as to maintain a constant distance between the focal spot and the detector notwithstanding the variation in the location of the focal spot.

7. The method according to claim 4, wherein irradiating the sample comprises introducing a beam-limiting optic into the beam, and wherein assessing the effect comprises finding the variation in the location due to introduction of the beam-limiting optic.

8. The method according to claim 7, wherein introducing the beam-limiting optic comprises positioning a knife edge so as to intercept the beam in a position adjacent to the focal spot.

9. The method according to claim 8, wherein positioning the knife edge comprises adjusting a position of the knife edge, and wherein finding the variation in the location comprises measuring the variation as a function of the position of the knife edge.

10. The method according to claim 9, wherein adjusting the position comprises adjusting a height of the knife edge relative to the surface of the sample, and wherein correcting the spectrum comprises determining a correction to apply to the spectrum responsively to the height.

11. The method according to claim 9, wherein adjusting the position comprises adjusting a lateral position of the knife edge relative to the beam, and wherein correcting the spectrum comprises selecting the lateral position so as to minimize the effect of the non-uniformity.

12. The method according to claim 4, wherein measuring the distribution of the X-rays comprises recording measurement values as a function of the elevation angle, and wherein correcting the spectrum comprises modifying the measurement values to account for the variation in the location of the focal spot.

13. The method according to claim 12, wherein assessing the variation comprises determining an effective variation in the location of the focal spot as a function of the elevation angle, and wherein modifying the measurement values comprises adjusting a mapping of the measurement values to elevation angles responsively to the effective variation.

14. The method according to claim 2, wherein irradiating the sample comprises introducing a beam-limiting optic into the beam, and wherein assessing the effect comprises measuring a variation in the beam as a function of the elevation angle due to introduction of the beam-limiting optic.

15. The method according to claim 14, wherein irradiating the sample comprises directing the beam to impinge on the sample at a focal location, and wherein introducing the beam-limiting optic comprises positioning a knife edge so as to intercept the beam in a position adjacent to the focal location.

16. The method according to claim 15, wherein positioning the knife edge comprises adjusting a height of the knife edge relative to the surface of the sample, and wherein correcting the spectrum comprises determining a correction to apply to the spectrum responsively to the height.

17. The method according to claim 15, wherein positioning the knife edge comprises adjusting a lateral position of the knife edge relative to the beam, and wherein correcting the spectrum comprises selecting the lateral position so as to minimize the effect of the non-uniformity.

18. The method according to claim 14, wherein assessing the effect comprises determining a correction factor as a function of the elevation angle responsively to the measured variation, and wherein correcting the spectrum comprises applying the correction factor to the spectrum.

19. The method according to claim 18, wherein determining the correction factor comprises:
    directing the beam toward a detector array comprising a plurality of detector elements;
    making a first measurement of a flux of the X-rays that is incident on each of the detector elements with the beam-limiting optic in a first position;
    making a second measurement of the flux of the X-rays that is incident on each of the detector elements with the beam-limiting optic in a second position; and
    comparing the first and second measurements in order to determine the correction factor.

20. The method according to claim 19, wherein measuring the distribution of the X-rays that are reflected from the sample comprises measuring the distribution using the detector array with the beam-limiting optic in the first position.

21. The method according to claim 20, wherein making the first and second measurements comprises removing the sample from the beam of X-rays so that the beam is directly incident on the detector array.

22. The method according to claim 20, wherein making the first and second measurements comprises introducing a reflective surface into the beam at a location of the sample so that the X-rays are reflected onto the detector array.

23. The method according to claim 1, wherein irradiating the sample comprises introducing a beam-limiting optic into the beam, and wherein assessing the effect comprises measuring a variation in the beam due to introduction of the beam-limiting optic.

24. The method according to claim 23, wherein assessing the effect comprises determining a correction vector responsively to the measured variation, and wherein correcting the spectrum comprises applying the correction vector to the spectrum.

25. The method according to claim 24, wherein determining the correction vector comprises:
    directing the beam toward a detector array comprising a plurality of detector elements;
    making a first measurement of a flux of the X-rays that is incident on each of the detector elements with the beam-limiting optic in a first position;
    making a second measurement of the flux of the X-rays that is incident on each of the detector elements with the beam-limiting optic in a second position; and
    comparing the first and second measurements in order to determine the correction vector.

26. The method according to claim 25, wherein the detector array has an axis, and wherein the method comprises rotating the array so as to position the axis perpendicular to a surface of the sample.

27. The method according to claim 1, wherein measuring the distribution comprises:
    providing a tilt map indicating a characteristic tilt angle of the sample at multiple points over a surface of the sample;
    determining, based on the tilt map, a local tilt angle at a location on the sample upon which the beam of X-rays is incident; and
    correcting the spectrum responsively to the local tilt angle.

28. A method for inspection of a sample, comprising:
    irradiating a surface of the sample with a beam of X-rays;
    measuring a distribution of the X-rays that are emitted from the sample responsively to the beam using a detector array, which has an axis and comprises a plurality of detector elements arranged along the axis; and
    rotating the detector array so as to position the axis perpendicular to the surface of the sample.

29. The method according to claim 28, wherein measuring the distribution comprises measuring the distribution of the X-rays that are reflected from the sample as a function of an elevation angle relative to a surface of the sample.

30. The method according to claim 29, wherein measuring the distribution of the X-rays comprises observing an oscillatory pattern in the X-rays emitted as a function of the elevation angle, and rotating the detector array comprises aligning the detector array responsively to the oscillatory pattern.

31. The method according to claim 30, wherein aligning the detector array comprises rotating the detector array so as to maximize a contrast of the oscillatory pattern.

32. The method according to claim 28, wherein irradiating the surface comprises directing the beam toward the surface at a grazing incidence, and wherein measuring the distribution comprises detecting a transition in the distribution corresponding to a plane of the surface of the sample, and wherein rotating the detector array comprises aligning the detector array responsively to the transition.

33. The method according to claim 30, wherein aligning the detector array comprises rotating the detector array so as to maximize a sharpness of the transition.

34. A method for inspection of a sample, comprising:
    providing a tilt map, indicating a characteristic tilt angle of a reference surface at multiple points on the reference surface;
    acquiring an X-ray reflectance (XRR) spectrum at a location on a sample;
    determining an estimated tilt angle of the location on the sample based on the tilt map; and
    correcting the XRR spectrum responsively to the estimated tilt angle.

35. The method according to claim 34, wherein providing the tilt map comprises measuring the characteristic tilt angle of the reference surface at each of the multiple points.

36. The method according to claim 35, wherein acquiring the XRR spectrum comprises mounting the sample on a mounting assembly, and wherein measuring the characteristic tilt angle comprises mounting the reference surface on the mounting assembly, and measuring the characteristic tilt angle while the reference surface is on the mounting assembly.

37. The method according to claim 36, wherein measuring the characteristic tilt angle comprises rotating and translating the mounting assembly, and taking measurements of the tilt angle as a function of rotation and translation.

38. The method according to claim 34, wherein determining the estimated tilt angle comprises finding the estimated tilt angle by interpolation along a curve in the tilt map.

39. The method according to claim 34, wherein the sample comprises a semiconductor wafer.

40. A method for inspection of a sample, comprising:
focusing a beam of X-rays onto a focal location on the sample;
positioning a knife edge so as to intercept the beam in a position adjacent to the focal location;
measuring a distribution of the X-rays that are emitted from the sample responsively to the beam and to the position of the knife edge; and
adjusting the position of the knife edge responsively to the distribution.

41. The method according to claim 40, wherein adjusting the position comprises adjusting a lateral location of the knife edge relative to the beam.

42. The method according to claim 41, wherein measuring the distribution comprises measuring a variation in the distribution of the X-rays as a function of a vertical location of the knife edge relative to a surface of the sample at each of a plurality of lateral locations of the knife edge, and wherein adjusting the lateral location comprises choosing the lateral location responsively to the variation in the distribution.

43. The method according to claim 42, wherein choosing the lateral location comprises finding the lateral location that minimizes the variation in the distribution as a function of the vertical location.

44. The method according to claim 40, wherein adjusting the position comprises adjusting a skew angle of the knife edge relative to a surface of the sample.

45. A method for inspection of a sample, comprising:
irradiating the sample with a beam of X-rays over a range of angles of incidence;
positioning a shutter so as to intercept the beam at a predetermined angle;
measuring a distribution of the X-rays that are emitted from the sample responsively to the beam, thereby generating an X-ray spectrum, which includes a shadow of the shutter;
determining a tilt angle of the sample responsively to an angular position of the shadow in the spectrum; and
processing the spectrum responsively to the tilt angle.

46. The method according to claim 45, wherein measuring the distribution of the X-rays comprises measuring the distribution of the X-rays that are reflected from the sample as a function of the elevation angle relative to a surface of the sample, and wherein processing the spectrum comprises calibrating the spectrum with respect to the tilt angle.

47. The method according to claim 46, wherein the predetermined angle is below a critical angle of the sample for total external reflection.

48. The method according to claim 45, wherein measuring the distribution comprises finding a current angular position of the shadow, and wherein determining the tilt angle comprises comparing the current angular position to a reference angular position of the shadow, which is indicative of a zero tilt angle.

49. The method according to claim 48, wherein comparing the current angular position to the reference angular position comprises finding a difference between the current and reference angular positions, and determining the tilt angle of the sample to be equal to half the difference.

50. A method for inspection of a sample, comprising:
focusing a beam of X-rays onto a focal location on the sample;
measuring a distribution of the X-rays that are reflected from the sample responsively to the beam, thereby generating an actual reflectance spectrum;
estimating a spot size of the beam on the sample at the focal location;
computing a simulated reflectance spectrum of the sample responsively to the spot size; and
fitting the simulated reflectance spectrum to the actual reflectance spectrum in order to determine one or more properties of the sample.

51. The method according to claim 50, wherein computing the simulated reflectance spectrum comprises blurring the simulated reflectance spectrum based on an angular spread of the reflected X-rays due to the spot size.

52. The method according to claim 51, wherein estimating the spot size comprises assessing a variation in an effective spot size of the beam as a function of an elevation angle relative to the sample, and wherein blurring the simulated reflectance spectrum comprises applying a variable blur to the simulated reflectance spectrum responsively to the variation in the effective spot size.

53. The method according to claim 50, wherein focusing the beam of X-rays comprises positioning a beam-limiting optic in the beam, and wherein estimating the spot size comprises determining the spot size as a function of a position of the beam-limiting optic relative to a surface of the sample.

54. The method according to claim 50, wherein fitting the simulated reflectance spectrum to the actual reflectance spectrum comprises determining at least one of a thickness, a density and a surface quality of a surface layer of the sample.

55. Apparatus for inspection of a sample, comprising:
an X-ray source, which irradiates the sample with a beam of X-rays;
a detector assembly, which measures a distribution of the X-rays that are emitted from the sample responsively to the beam, thereby generating an X-ray spectrum; and
a signal processor, which assesses an effect on the spectrum of a non-uniformity of the beam to correct the spectrum responsively to the effect.

56. The apparatus according to claim 55, wherein the detector assembly measures the distribution of the X-rays that are reflected from the sample as a function of an elevation angle relative to a surface of the sample.

57. The apparatus according to claim 56, wherein the X-ray source focuses the beam so that the X-rays converge on the sample over a range of incidence angles.

58. The apparatus according to claim 57, wherein the X-ray source focuses the beam so as to form a focal spot on the surface of the sample, and wherein the signal processor assesses a variation in a location of the focal spot.

59. The apparatus according to claim 58, wherein the detector assembly comprises a detector and an alignment mechanism, which adjusts a position of the detector responsively to the variation in the location of the focal spot.

60. The apparatus according to claim 59, wherein the alignment mechanism aligns the detector so as to maintain a constant distance between the focal spot and the detector notwithstanding the variation in the location of the focal spot.

61. The apparatus according to claim 58, and comprising a beam-limiting optic introduced into the beam, wherein the signal processor assesses the variation in the location due to introduction of the beam-limiting optic.

62. The apparatus according to claim 61, wherein the beam-limiting optic comprises a knife edge, which intercepts the beam in a position adjacent to the focal spot.

63. The apparatus according to claim 62, and comprising a positioning assembly, which adjusts a position of the knife edge, and wherein the signal processor assesses the variation as a function of the position of the knife edge.

64. The apparatus according to claim 63, wherein the positioning assembly adjusts a height of the knife edge relative to the surface of the sample, and wherein the signal processor determines a correction to apply to the spectrum responsively to the height.

65. The apparatus according to claim 63, wherein the positioning assembly adjusts a lateral position of the knife edge relative to the beam, and wherein the signal processor selects the lateral position so as to minimize the effect of the non-uniformity.

66. The apparatus according to claim 58, wherein the signal processor records measured values of intensity of the X-rays at a function of the elevation angle, and corrects the measured values to account for the variation in the location of the focal spot.

67. The apparatus according to claim 66, wherein the signal processor determines an effective variation in the location of the focal spot as a function of the elevation angle, and adjusts a mapping of the measurement values to elevation angles responsively to the effective variation.

68. The apparatus according to claim 56, and comprising a beam-limiting optic introduced into the beam, wherein the signal processor assesses a variation in the beam as a function of the elevation angle due to introduction of the beam-limiting optic.

69. The apparatus according to claim 68, wherein the X-ray source directs the beam to impinge on the sample at a focal location, and wherein the beam-limiting optic comprises a knife edge, which intercepts the beam in a position adjacent to the focal location.

70. The apparatus according to claim 69, and comprising a positioning assembly, which adjusts a height of the knife edge relative to the surface of the sample, and wherein the signal processor applies a correction to the spectrum responsively to the height.

71. The apparatus according to claim 69, and comprising a positioning assembly, which adjusts a lateral position of the knife edge relative to the beam, and wherein the signal processor selects the lateral position so as to minimize the effect of the non-uniformity.

72. The apparatus according to claim 68, wherein the signal processor determines a correction factor as a function of the elevation angle responsively to the variation, and applies the correction factor in order to correct to the spectrum.

73. The apparatus according to claim 72, wherein the detector assembly comprises a detector array, which comprises a plurality of detector elements, and wherein the signal processor determines the correction factor by comparing a first measurement of a flux of the X-rays that is incident on each of the detector elements with the beam-limiting optic in a first position with a second measurement of the flux of the X-rays that is incident on each of the detector elements with the beam-limiting optic in a second position.

74. The apparatus according to claim 73, wherein the detector array measures the distribution of the X-rays that are reflected from the sample with the beam-limiting optic in the first position.

75. The apparatus according to claim 74, wherein the sample is removed from the beam of X-rays while the first and second measurements are made so that the beam is directly incident on the detector array.

76. The apparatus according to claim 74, wherein a reflective surface is introduced into the beam at a location of the sample while the first and second measurements are made so that the X-rays are reflected onto the detector array.

77. The apparatus according to claim 55, and comprising a beam-limiting optic introduced into the beam, wherein the signal processor measures a variation in the beam due to introduction of the beam-limiting optic.

78. The apparatus according to claim 77, wherein the signal processor determines a correction vector responsively to the variation, and corects the spectrum by applying the correction vector to the spectrum.

79. The apparatus according to claim 78, wherein the detector assembly comprises a detector array, which comprises a plurality of detector elements, and wherein the signal processor determines the correction vector by comparing a first measurement of a flux of the X-rays that is incident on each of the detector elements with the beam-limiting optic in a first position with a second measurement of the flux of the X-rays that is incident on each of the detector elements with the beam-limiting optic in a second position.

80. The apparatus according to claim 79, wherein the detector array has an axis, and wherein the detector assembly comprises an alignment mechanism, which rotates the array so as to position the axis perpendicular to a surface of the sample.

81. The apparatus according to claim 55, wherein the signal processor receives a tilt map indicating a characteristic tilt angle of the sample at multiple points over a surface of the sample, and determines, based on the tilt map, a local tilt angle at a location on the sample upon which the beam of X-rays is incident, and corrects the spectrum responsively to the local tilt angle.

82. Apparatus for inspection of a sample, comprising:
an X-ray source, which irradiates a surface of the sample with a beam of X-rays;
a detector array, which has an axis and comprises a plurality of detector elements arranged along the axis, and which measures a distribution of the X-rays that are emitted from the sample responsively to the beam; and
an alignment mechanism, which rotates the detector array so as to position the axis perpendicular to the surface of the sample.

83. The apparatus according to claim 82, wherein the detector array measures the distribution of the X-rays that are reflected from the sample as a function of an elevation angle relative to a surface of the sample.

84. The apparatus according to claim 83, wherein the distribution of the X-rays comprises an oscillatory pattern as a function of the elevation angle, and comprising a signal processor, which controls the alignment mechanism so as to rotate the detector array responsively to the oscillatory pattern.

85. The apparatus according to claim 84, wherein the signal processor causes the alignment mechanism to rotate the detector array so as to maximize a contrast of the oscillatory pattern.

86. The apparatus according to claim 82, wherein the X-ray source directs the beam toward the surface at a grazing incidence, and comprising a signal processor, which detects a transition in the distribution corresponding to a plane of the surface of the sample, and controls the alignment mechanism so as to rotate the detector array responsively to the transition.

87. The apparatus according to claim 86, wherein the signal processor causes the alignment mechanism to rotate the detector array so as to maximize a sharpness of the transition.

88. Apparatus for inspection of a sample, comprising:
an X-ray source, which irradiates a sample with a beam of X-rays;

a detector, which receives the X-rays reflected from a location on the sample so as to acquire an X-ray reflectance (XRR) spectrum of the sample at the location; and a signal processor, which receives a tilt map, indicating a characteristic tilt angle of a reference surface at multiple points on the reference surface, and determines an estimated tilt angle of the first location on the sample based on the tilt map, and corrects the XRR spectrum responsively to the estimated tilt angle.

89. The apparatus according to claim 88, wherein the tilt map is produced by measuring the characteristic tilt angle of the reference surface at each of the multiple points.

90. The apparatus according to claim 89, and comprising a mounting assembly, on which the sample is mounted while acquiring the XRR spectrum, and wherein the characteristic tilt angle at each of the multiple points is measured by mounting the reference surface on the mounting assembly, and measuring the characteristic tilt angle while the reference surface is on the mounting assembly.

91. The apparatus according to claim 90, wherein the mounting assembly rotates and translates the sample, and wherein the tilt map is indicative of the tilt angle as a function of rotation and translation of the sample.

92. The apparatus according to claim 88, wherein the signal processor finds the estimated tilt angle by interpolation along a curve in the tilt map.

93. The apparatus according to claim 88, wherein the sample comprises a semiconductor wafer.

94. Apparatus for inspection of a sample, comprising:
an X-ray source, which focuses a beam of X-rays onto a focal location on the sample;
a knife edge;
a positioning assembly, which positions the knife edge so as to intercept the beam in a position adjacent to the focal location;
a detector assembly, which measures a distribution of the X-rays that are emitted from the sample, thereby generating an X-ray spectrum; and
a signal processor, which receives the X-ray spectrum, and assesses an effect of the position of the knife edge on the X-ray spectrum, and causes the positioning assembly to adjust the position of the knife edge responsively to the effect.

95. The apparatus according to claim 94, wherein the positioning assembly adjusts a lateral location of the knife edge relative to the beam under control of the signal processor.

96. The apparatus according to claim 95, wherein the signal processor assesses a variation in the distribution of the X-rays as a function of a vertical location of the knife edge relative to a surface of the sample at each of a plurality of lateral locations of the knife edge, and chooses the lateral location responsively to the variation in the distribution.

97. The apparatus according to claim 96, wherein the signal processor chooses the lateral location that minimizes the variation in the distribution as a function of the vertical location.

98. The apparatus according to claim 94, wherein the positioning assembly adjusts a skew angle of the knife edge relative to a surface of the sample under control of the signal processor.

99. Apparatus for inspection of a sample, comprising:
an X-ray source, which irradiates the sample with a beam of X-rays over a range of angles of incidence;
a shutter, which is positioned so as to intercept the beam at a predetermined angle;
a detector assembly, which measures a distribution of the X-rays that are emitted from the sample responsively to the beam, thereby generating an X-ray spectrum, which includes a shadow of the shutter; and
a signal processor, which determines a tilt angle of the sample responsively to an angular position of the shadow in the spectrum, and to process the spectrum responsively to the tilt angle.

100. The apparatus according to claim 99, wherein the detector assembly measures the distribution of the X-rays that are reflected from the sample as a function of the elevation angle relative to a surface of the sample, and wherein the signal processor calibrates the spectrum with respect to the tilt angle.

101. The apparatus according to claim 100, wherein the predetermined angle is below a critical angle of the sample for total external reflection.

102. The apparatus according to claim 99, wherein the signal processor finds a current angular position of the shadow in the spectrum, and to determine the tilt angle by comparing the current angular position to a reference angular position of the shadow, which is indicative of a zero tilt angle.

103. The apparatus according to claim 102, wherein the signal processor finds a difference between the current and reference angular positions, and determines the tilt angle of the sample to be equal to half the difference.

104. Apparatus for inspection of a sample, comprising:
an X-ray source, which focuses a beam of X-rays onto a focal location on the sample;
a detector assembly, which measures a distribution of the X-rays that are reflected from the sample responsively to the beam, thereby generating an actual reflectance spectrum; and
a signal processor, which estimates a spot size of the beam on the sample at the focal location, computes a simulated reflectance spectrum of the sample responsively to the spot size, and fits the simulated reflectance spectrum to the actual reflectance spectrum in order to determine one or more properties of the sample.

105. The apparatus according to claim 104, wherein the signal processor blurs the simulated reflectance spectrum based on an angular spread of the reflected X-rays due to the spot size.

106. The apparatus according to claim 105, wherein the signal processor assesses a variation in an effective spot size of the beam as a function of an elevation angle relative to the sample, and applies a variable blur to the simulated reflectance spectrum responsively to the variation in the effective spot size.

107. The apparatus according to claim 104, and comprising a beam-limiting optic in the beam of the X-rays, wherein the signal processor estimates the spot size as a function of a position of the beam-limiting optic relative to a surface of the sample.

108. The apparatus according to claim 104, wherein the signal processor fits the simulated reflectance spectrum to the actual reflectance spectrum so as to determine at least one of a thickness, a density and a surface quality of a surface layer of the sample.

* * * * *